(12) United States Patent
Sinnott et al.

(10) Patent No.: US 9,357,997 B2
(45) Date of Patent: Jun. 7, 2016

(54) SUTURE PASSER AND METHOD

(75) Inventors: M. Mary Sinnott, Logan, UT (US); Thomas Wade Fallin, Hyde Park, UT (US)

(73) Assignee: Smith & Nephew, Inc., Memphis, TN (US)

(*) Notice: Subject to any disclaimer, the term of this patent is extended or adjusted under 35 U.S.C. 154(b) by 293 days.

(21) Appl. No.: 13/527,424

(22) Filed: Jun. 19, 2012

(65) Prior Publication Data
US 2013/0012965 A1 Jan. 10, 2013

(51) Int. Cl.
*A61B 17/04* (2006.01)
*A61B 17/12* (2006.01)
*A61B 17/06* (2006.01)

(52) U.S. Cl.
CPC ......... *A61B 17/0469* (2013.01); *A61B 17/0483* (2013.01); *A61B 17/0491* (2013.01); *A61B 2017/06042* (2013.01)

(58) Field of Classification Search
CPC . A61B 17/04; A61B 17/0469; A61B 17/0491
USPC .................................................. 606/144, 147
See application file for complete search history.

(56) References Cited

U.S. PATENT DOCUMENTS

| | | |
|---|---|---|
| 919,138 A | 4/1909 | Drake et al. |
| 1,037,864 A | 9/1912 | Carlson et al. |
| 1,449,087 A | 3/1923 | Bugbee |
| 1,635,066 A | 7/1927 | Wells |
| 1,815,725 A | 7/1931 | Pilling et al. |
| 1,822,330 A | 9/1931 | Ainslie |
| 1,856,721 A | 5/1932 | Nagelmann |
| 1,918,700 A | 7/1933 | Harris |
| 1,933,024 A | 10/1933 | Nagelmann |
| 1,981,651 A | 11/1934 | Logan |

(Continued)

FOREIGN PATENT DOCUMENTS

| | | |
|---|---|---|
| GB | 2475491 A | 5/2011 |
| WO | WO 03/007799 A2 | 1/2003 |

(Continued)

OTHER PUBLICATIONS

2008 Arthrex Inc., "*The Arthrex Scorpion*" 6 pages.

(Continued)

*Primary Examiner* — Melanie Tyson
(74) *Attorney, Agent, or Firm* — Taft Stettinius & Hollister LLP

(57) ABSTRACT

Instruments and techniques to pass a suture, particularly in instances where access to confined spaces and the ability to pass a suture through difficult to penetrate materials are needed. According to certain embodiments, a suture passer is provided including a housing, a needle assembly, and a barrel assembly. The needle assembly may include a needle that is displaceable along a linear motion axis of the housing, and which is adapted to engage a suture. The barrel assembly may include a foot having an opening in a proximal facing surface to receive passage of the needle. The foot may include an elbow having proximal and distal portions, with the proximal portion having a distal facing surface that extends along a proximal portion axis diverging distally away from the motion axis, and the distal portion extending distally from the proximal portion and having a proximal facing surface that extends along a distal portion axis that is arranged transverse to the motion axis.

25 Claims, 33 Drawing Sheets

(56) References Cited

U.S. PATENT DOCUMENTS

| | | |
|---|---|---|
| 2,240,330 A | 4/1941 | Flagg et al. |
| 2,269,963 A | 1/1942 | Wappler |
| 2,286,578 A | 6/1942 | Sauter |
| 2,301,500 A | 11/1942 | Anderson |
| 2,577,240 A | 12/1951 | Findley |
| 2,697,433 A | 12/1954 | Zehnder |
| 2,738,790 A | 3/1956 | Todt, Sr. et al. |
| 3,013,559 A | 12/1961 | Thomas |
| 3,090,386 A | 5/1963 | Curtis |
| 3,470,875 A | 10/1969 | Johnson |
| 3,638,653 A | 2/1972 | Berry |
| 3,840,017 A | 10/1974 | Violante |
| 3,842,840 A | 10/1974 | Schweizer |
| 3,946,740 A | 3/1976 | Bassett |
| 4,109,658 A | 8/1978 | Hughes |
| 4,164,225 A | 8/1979 | Johnson et al. |
| 4,172,458 A | 10/1979 | Pereyra |
| 4,224,947 A | 9/1980 | Fukuda |
| 4,345,601 A | 8/1982 | Fukuda |
| 4,373,530 A | 2/1983 | Kilejian |
| 4,406,237 A | 9/1983 | Eguchi et al. |
| 4,417,532 A | 11/1983 | Yasukata |
| 4,493,323 A | 1/1985 | Albright et al. |
| 4,596,249 A | 6/1986 | Freda et al. |
| 4,686,972 A | 8/1987 | Kurland |
| 4,739,751 A | 4/1988 | Sapega et al. |
| 4,781,182 A | 11/1988 | Purnell et al. |
| 4,823,780 A | 4/1989 | Odensten et al. |
| 4,836,205 A | 6/1989 | Barrett |
| 4,883,048 A | 11/1989 | Purnell et al. |
| 4,890,615 A | 1/1990 | Caspari et al. |
| 4,923,461 A | 5/1990 | Caspari et al. |
| 4,929,247 A | 5/1990 | Rayhack |
| 4,935,027 A | 6/1990 | Yoon |
| 4,957,498 A | 9/1990 | Caspari et al. |
| 4,964,861 A | 10/1990 | Agee et al. |
| 5,042,983 A | 8/1991 | Rayhack |
| 5,059,201 A | 10/1991 | Asnis |
| 5,112,335 A | 5/1992 | Laboureau et al. |
| 5,112,337 A | 5/1992 | Paulos et al. |
| 5,176,685 A | 1/1993 | Rayhack |
| 5,217,471 A | 6/1993 | Burkhart |
| 5,222,977 A | 6/1993 | Esser |
| 5,281,237 A | 1/1994 | Gimpelson |
| 5,312,422 A | 5/1994 | Trott |
| 5,312,423 A | 5/1994 | Rosenbluth |
| 5,318,577 A | 6/1994 | Li |
| 5,336,229 A | 8/1994 | Noda |
| 5,397,325 A | 3/1995 | Della Badia et al. |
| 5,431,666 A | 7/1995 | Sauer et al. |
| 5,433,722 A | 7/1995 | Sharpe et al. |
| 5,439,467 A | 8/1995 | Benderev et al. |
| 5,454,823 A | 10/1995 | Richardson et al. |
| 5,462,562 A | 10/1995 | Elkus |
| 5,474,565 A | 12/1995 | Trott |
| 5,499,991 A | 3/1996 | Garman et al. |
| 5,520,693 A | 5/1996 | McGuire et al. |
| 5,522,820 A | 6/1996 | Caspari et al. |
| 5,544,664 A | 8/1996 | Benderev et al. |
| 5,562,686 A | 10/1996 | Sauer et al. |
| 5,571,119 A | 11/1996 | Atala |
| 5,573,542 A | 11/1996 | Stevens |
| 5,575,801 A | 11/1996 | Habermeyer et al. |
| 5,618,290 A | 4/1997 | Toy et al. |
| 5,632,752 A | 5/1997 | Buelna |
| 5,645,552 A | 7/1997 | Sherts |
| 5,662,663 A | 9/1997 | Shallman |
| 5,662,664 A | 9/1997 | Gordon et al. |
| 5,665,096 A | 9/1997 | Yoon |
| 5,690,653 A | 11/1997 | Richardson et al. |
| 5,713,908 A | 2/1998 | Jameel et al. |
| 5,713,910 A | 2/1998 | Gordon et al. |
| 5,730,747 A | 3/1998 | Ek et al. |
| 5,741,277 A | 4/1998 | Gordon et al. |
| 5,741,278 A | 4/1998 | Stevens |
| 5,741,279 A | 4/1998 | Gordon et al. |
| 5,741,281 A | 4/1998 | Martin |
| 5,766,186 A | 6/1998 | Faraz et al. |
| 5,776,150 A | 7/1998 | Nolan et al. |
| 5,792,153 A | 8/1998 | Swain et al. |
| 5,797,927 A | 8/1998 | Yoon |
| 5,860,992 A | 1/1999 | Daniel et al. |
| 5,871,488 A | 2/1999 | Tovey et al. |
| 5,902,311 A | 5/1999 | Andreas et al. |
| 5,904,692 A | 5/1999 | Steckel et al. |
| 5,908,426 A | 6/1999 | Pierce |
| 5,919,199 A | 7/1999 | Mers Kelly et al. |
| 5,921,994 A | 7/1999 | Andreas et al. |
| 5,928,252 A | 7/1999 | Steadman et al. |
| 5,947,982 A | 9/1999 | Duran |
| 5,968,050 A | 10/1999 | Torrie |
| 5,980,538 A | 11/1999 | Fuchs et al. |
| 5,984,933 A | 11/1999 | Yoon |
| 6,007,535 A | 12/1999 | Rayhack et al. |
| 6,022,360 A | 2/2000 | Reimels et al. |
| 6,036,699 A | 3/2000 | Adreas et al. |
| 6,051,006 A | 4/2000 | Shluzas et al. |
| 6,071,289 A | 6/2000 | Stefanchik et al. |
| 6,074,403 A | 6/2000 | Nord |
| 6,096,051 A | 8/2000 | Kortenbach et al. |
| 6,136,010 A | 10/2000 | Modesitt et al. |
| 6,143,004 A | 11/2000 | Davis et al. |
| 6,156,039 A | 12/2000 | Thal |
| 6,187,011 B1 | 2/2001 | Torrie |
| 6,197,035 B1 | 3/2001 | Loubens et al. |
| 6,217,592 B1 | 4/2001 | Freda et al. |
| 6,270,503 B1 | 8/2001 | Schmieding |
| 6,296,659 B1 | 10/2001 | Foerster |
| 6,332,889 B1 | 12/2001 | Sancoff et al. |
| 6,475,135 B1 | 11/2002 | Levy |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,582,453 B1 | 6/2003 | Tran et al. |
| 6,585,730 B1 | 7/2003 | Foerster |
| 6,605,096 B1 | 8/2003 | Ritchart |
| 6,723,107 B1 | 4/2004 | Skiba et al. |
| 6,725,082 B2 | 4/2004 | Sati et al. |
| 6,770,076 B2 | 8/2004 | Foerster |
| 6,770,084 B1 | 8/2004 | Bain et al. |
| 6,802,807 B2 | 10/2004 | Anderson et al. |
| 6,855,157 B2 | 2/2005 | Foerster et al. |
| 6,878,150 B1 | 4/2005 | McGuire et al. |
| 6,893,448 B2 | 5/2005 | O'Quinn et al. |
| 6,896,686 B2 | 5/2005 | Weber |
| 6,911,034 B2 | 6/2005 | Nobles et al. |
| 6,936,054 B2 | 8/2005 | Chu |
| 6,984,237 B2 | 1/2006 | Hatch et al. |
| 6,997,932 B2 | 2/2006 | Dreyfuss et al. |
| 7,025,770 B2 | 4/2006 | McGuire et al. |
| 7,083,638 B2 | 8/2006 | Foerster |
| 7,090,686 B2 | 8/2006 | Nobles et al. |
| 7,112,208 B2 | 9/2006 | Morris et al. |
| 7,118,583 B2 | 10/2006 | O'Quinn et al. |
| 7,122,040 B2 | 10/2006 | Hill |
| 7,198,631 B2 | 4/2007 | Kanner et al. |
| 7,232,448 B2 | 6/2007 | Battles et al. |
| 7,285,124 B2 | 10/2007 | Foerster |
| 7,297,145 B2 | 11/2007 | Woloszko et al. |
| 7,329,264 B2 | 2/2008 | Merves |
| 7,377,926 B2 | 5/2008 | Topper et al. |
| 7,449,024 B2 | 11/2008 | Stafford |
| 7,544,199 B2 | 6/2009 | Bain et al. |
| 7,572,265 B2 | 8/2009 | Stone et al. |
| 7,575,578 B2 | 8/2009 | Wetzler et al. |
| 7,585,305 B2 | 9/2009 | Dreyfuss |
| 7,608,084 B2 | 10/2009 | Oren et al. |
| 7,695,494 B2 | 4/2010 | Foerster |
| 7,717,912 B2 | 5/2010 | Woloszko et al. |
| 7,722,630 B1 | 5/2010 | Stone et al. |
| 7,727,256 B2 | 6/2010 | McGregor |
| 7,758,597 B1 | 7/2010 | Tran et al. |
| 7,771,438 B2 | 8/2010 | Dreyfuss et al. |

(56) References Cited

U.S. PATENT DOCUMENTS

| | | |
|---|---|---|
| 7,815,654 B2 | 10/2010 | Chu |
| 7,879,046 B2 | 2/2011 | Weinert et al. |
| 7,879,048 B2 | 2/2011 | Bain et al. |
| 7,883,519 B2 | 2/2011 | Oren et al. |
| 7,922,744 B2 | 4/2011 | Morris et al. |
| 7,963,972 B2 | 6/2011 | Foerster et al. |
| 7,972,344 B2 | 7/2011 | Murray et al. |
| 8,110,000 B2 | 2/2012 | Collins |
| 8,147,505 B2 | 4/2012 | Delli-Santi |
| 8,282,656 B2 | 10/2012 | Hart |
| 8,469,974 B2 | 6/2013 | Skinlo |
| 8,545,521 B2 | 10/2013 | McClurg |
| 8,647,354 B2 | 2/2014 | Domingo |
| 2001/0037119 A1 | 11/2001 | Schmieding |
| 2002/0147456 A1 | 10/2002 | Diduch et al. |
| 2002/0173800 A1 | 11/2002 | Dreyfuss et al. |
| 2003/0078599 A1* | 4/2003 | O'Quinn et al. ............... 606/144 |
| 2003/0078600 A1 | 4/2003 | O'Quinn et al. |
| 2003/0195528 A1 | 10/2003 | Ritchart |
| 2003/0216742 A1 | 11/2003 | Wetzler et al. |
| 2003/0220659 A1 | 11/2003 | Schmieding et al. |
| 2003/0233106 A1 | 12/2003 | Dreyfuss |
| 2004/0010273 A1 | 1/2004 | Diduch et al. |
| 2004/0015177 A1 | 1/2004 | Chu |
| 2004/0138682 A1 | 7/2004 | Onuki et al. |
| 2004/0199184 A1* | 10/2004 | Topper et al. ................. 606/144 |
| 2004/0249394 A1 | 12/2004 | Morris et al. |
| 2005/0165419 A1 | 7/2005 | Sauer et al. |
| 2005/0240226 A1 | 10/2005 | Foerster et al. |
| 2006/0052801 A1 | 3/2006 | Dreyfuss et al. |
| 2006/0241658 A1 | 10/2006 | Cerundolo |
| 2006/0271060 A1 | 11/2006 | Gordon |
| 2007/0060953 A1 | 3/2007 | Morris et al. |
| 2007/0088362 A1 | 4/2007 | Bonutti et al. |
| 2007/0118150 A1 | 5/2007 | Weber |
| 2007/0149986 A1 | 6/2007 | Morris et al. |
| 2007/0179524 A1 | 8/2007 | Weber et al. |
| 2007/0233128 A1 | 10/2007 | Schmieding et al. |
| 2008/0015594 A1 | 1/2008 | Ritchart et al. |
| 2008/0097482 A1 | 4/2008 | Bain et al. |
| 2009/0036905 A1 | 2/2009 | Schmieding |
| 2009/0062816 A1 | 3/2009 | Weber |
| 2009/0062819 A1 | 3/2009 | Burkhart et al. |
| 2009/0131956 A1 | 5/2009 | Dewey et al. |
| 2009/0222040 A1 | 9/2009 | Foerster |
| 2009/0222041 A1 | 9/2009 | Foerster |
| 2009/0254126 A1 | 10/2009 | Orbay et al. |
| 2009/0318965 A1 | 12/2009 | Burkhart |
| 2010/0057216 A1 | 3/2010 | Gannoe et al. |
| 2010/0137889 A1 | 6/2010 | Oren et al. |
| 2010/0152752 A1 | 6/2010 | Denove et al. |
| 2010/0191283 A1 | 7/2010 | Foerster et al. |
| 2010/0211082 A1 | 8/2010 | Sauer |
| 2010/0211083 A1 | 8/2010 | Sauer |
| 2010/0249806 A1 | 9/2010 | Oren et al. |
| 2010/0268256 A1 | 10/2010 | Dreyfuss et al. |
| 2010/0324563 A1 | 12/2010 | Green, II et al. |
| 2010/0331623 A1 | 12/2010 | Sauer |
| 2011/0009867 A1 | 1/2011 | Oren et al. |
| 2011/0028998 A1* | 2/2011 | Adams ............... A61B 17/0469 606/145 |
| 2011/0066165 A1* | 3/2011 | Skinlo ................ A61B 17/0469 606/145 |
| 2011/0144647 A1 | 6/2011 | Appenzeller et al. |
| 2011/0144666 A1 | 6/2011 | Egle |
| 2011/0208198 A1 | 8/2011 | Anderson et al. |
| 2011/0276064 A1 | 11/2011 | Henrichsen |
| 2012/0143220 A1 | 6/2012 | Morgan |
| 2012/0283750 A1 | 11/2012 | Saliman |
| 2012/0303046 A1 | 11/2012 | Stone |
| 2014/0180313 A1* | 6/2014 | Harrison ............... A61B 17/062 606/145 |

FOREIGN PATENT DOCUMENTS

| | | |
|---|---|---|
| WO | WO 2004/002324 A1 | 1/2004 |
| WO | 2008043380 A1 | 4/2008 |
| WO | 2008076559 A1 | 6/2008 |

OTHER PUBLICATIONS

Coughlin, et al. "Second MTP Joint Instability: Grading of the Deformity and Description of Surgical Repair of Capsular Insufficiency" The Physician and Sportmedicine, Sep. 3, 2011, 39(3):132-141.

Blitz, et al. *"Plantar Plate Repair of the Second Metatarsophalangeal Joint: Technique and Tips"* Journal of Foot & Ankle Surgery, 2004 43(4):266-270.

Fleming and Camasta, *"Plantar Plate Dysfunction"* Chapter 4, (2002) pp. 22-28, http://www.podiatryinstitute.com/pdfs/Update_2002/2002_04.pdf.

Gregg et al., *"Plantar Plate Repair and Weil Osteotomy for Metatarsophalangeal Joint Instability"* Foot and Ankle Surgery, (2007) 13:116-121.

Nery et al., *"Lesser Metatarsophalangeal Joint Instability: Prospective Evaluation and Repair of Plantar Plate and Capsular Insufficiency"* Foot and Ankle International, Apr. 2012 33(4):301-311.

European Patent Office, Supplementary Partial European Search Report, dated Apr. 1, 2015, 6 pages.

International Search Report; International Searching Authority; International PCT Application No. PCT/US2012/045584; Jan. 31, 2013; 3 pages.

Written Opinion; International Searching Authority; International PCT Application No. PCT/US2012/045584; Jan. 31, 2013; 4 pages.

International Peliminary Report on Patentability; The International Bureau of WIPO; International PCT Applicaton No. PCT/US2012/045584; Jan. 14, 2014; 5 pages.

Supplementary Partial European Search Report; European Patent Office; European Patent Application No. 12810809.9; Apr. 1, 2015; 6 pages.

Extended European Search Report; European Patent Office; European Application No. 12810809.9; Feb. 15, 2016; 21 pages.

* cited by examiner

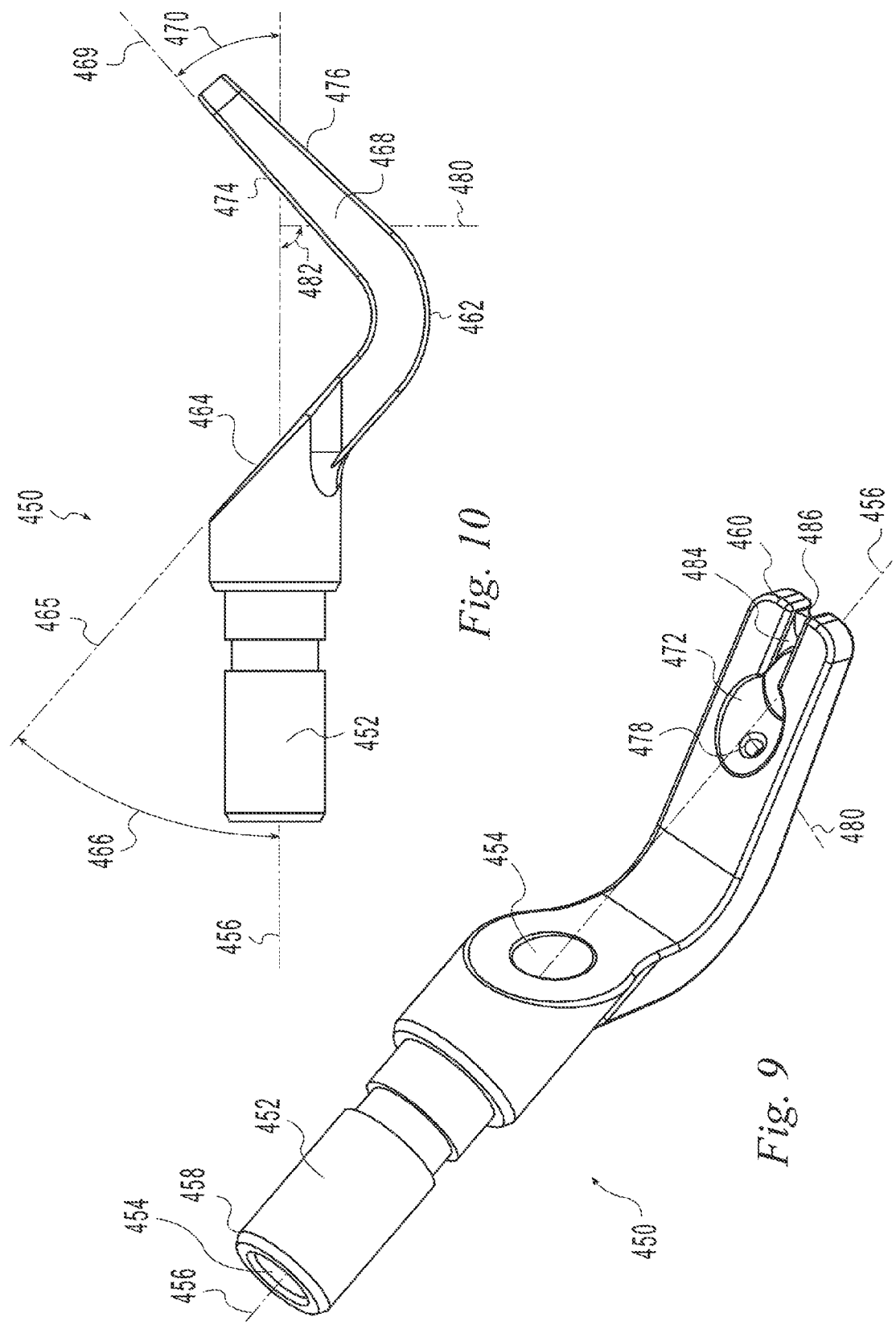

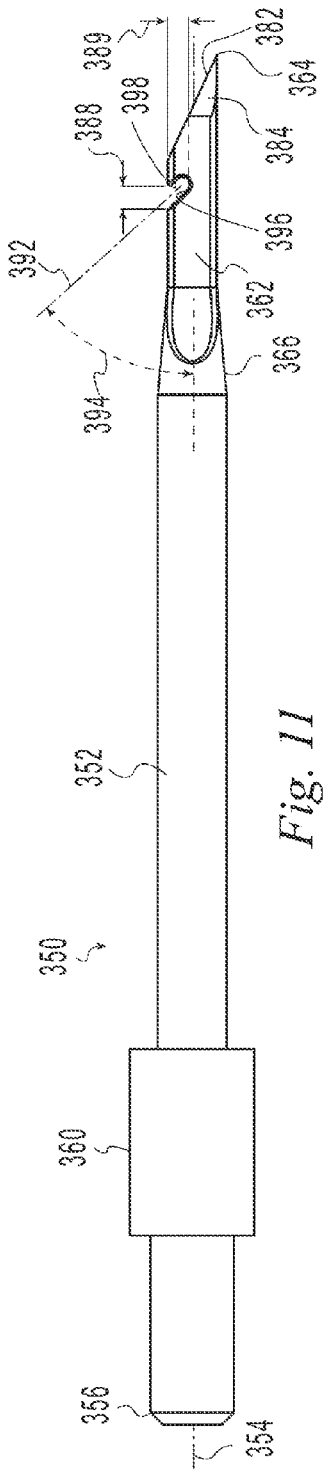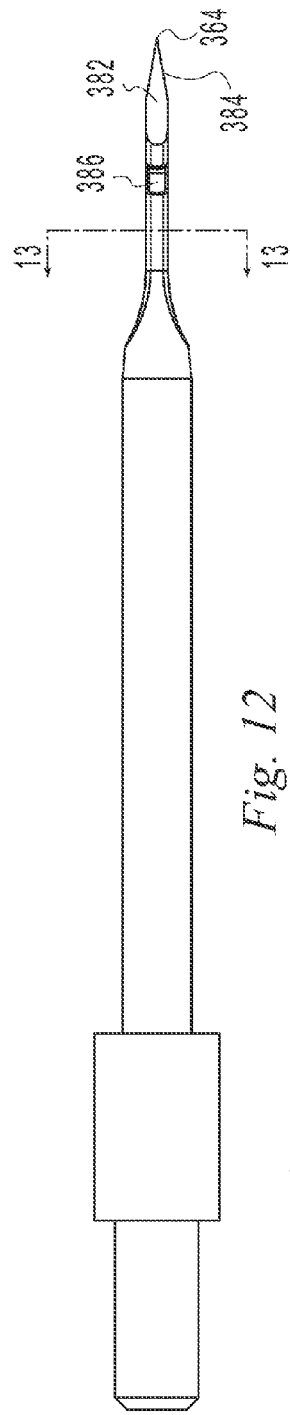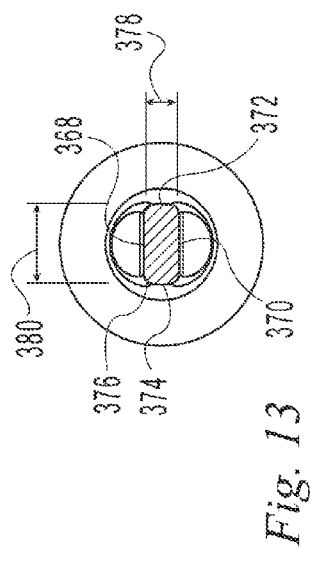

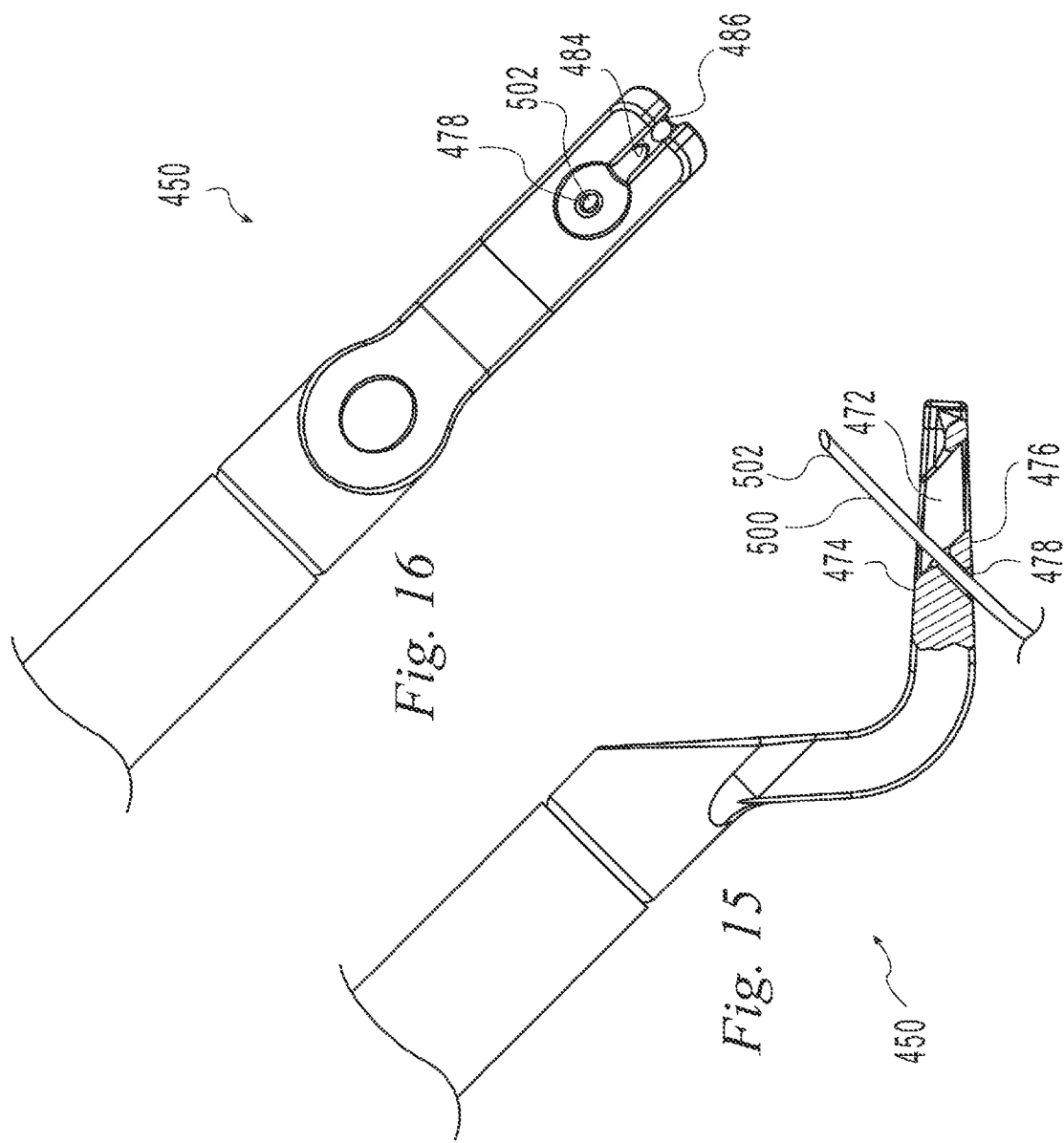

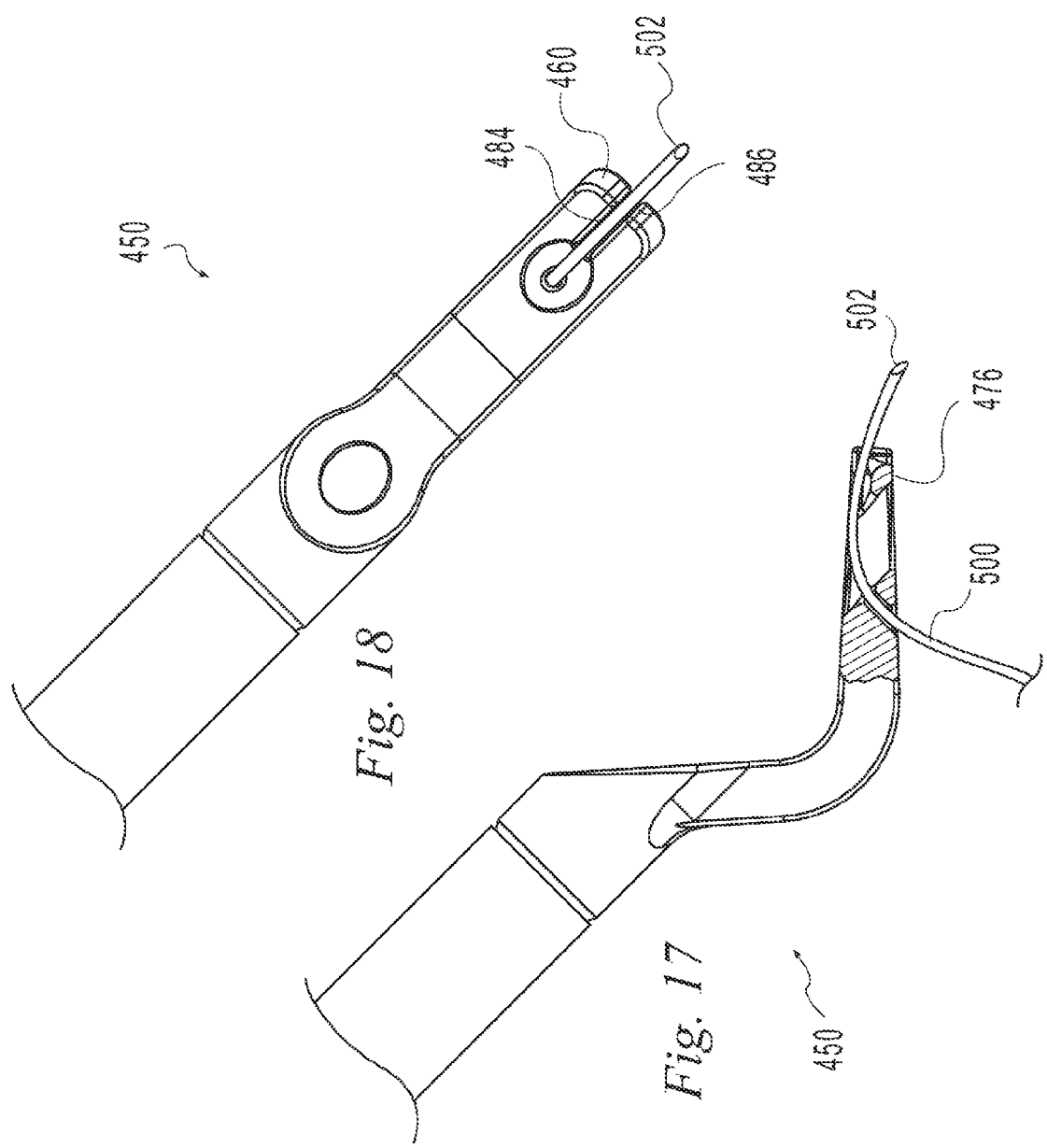

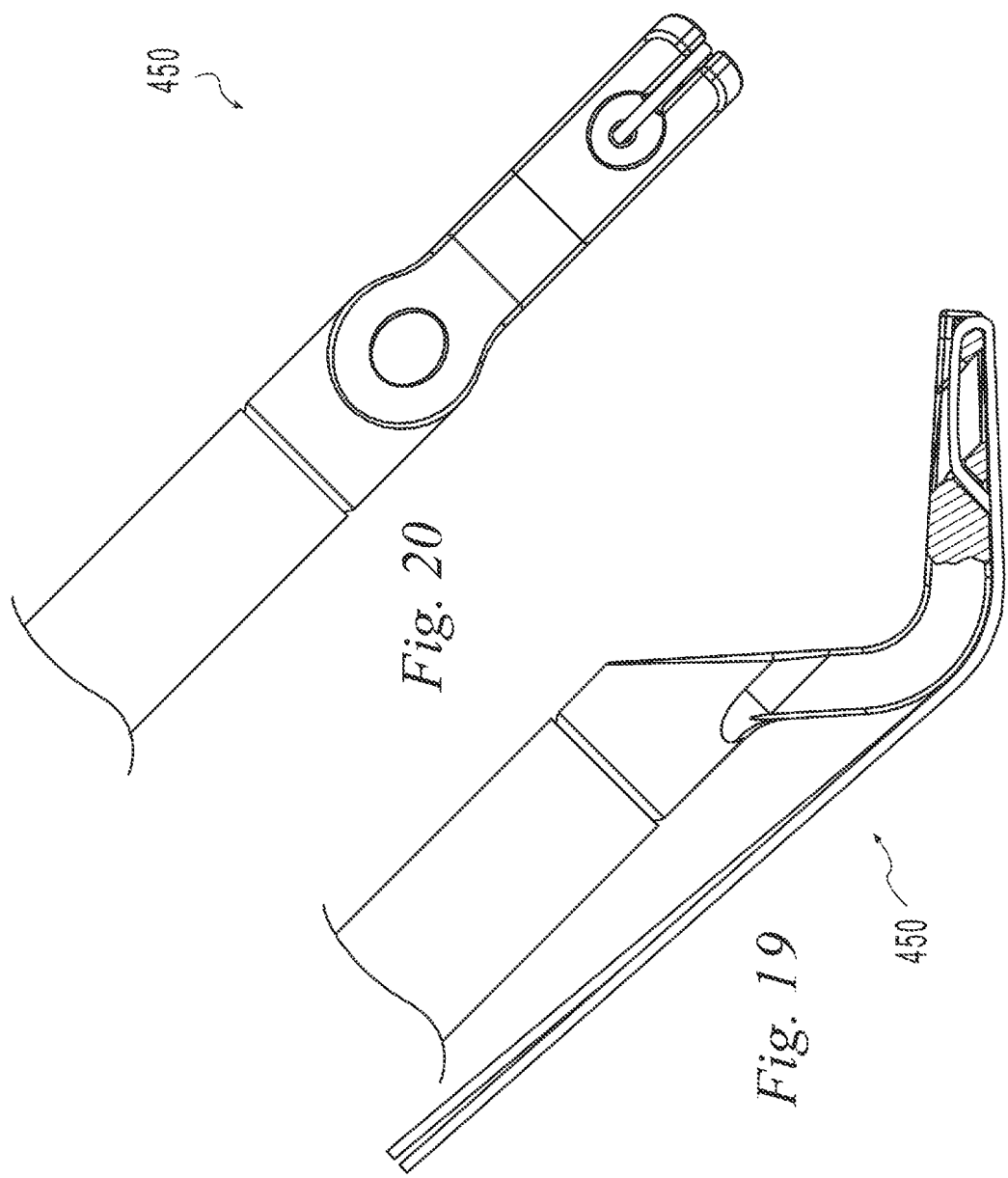

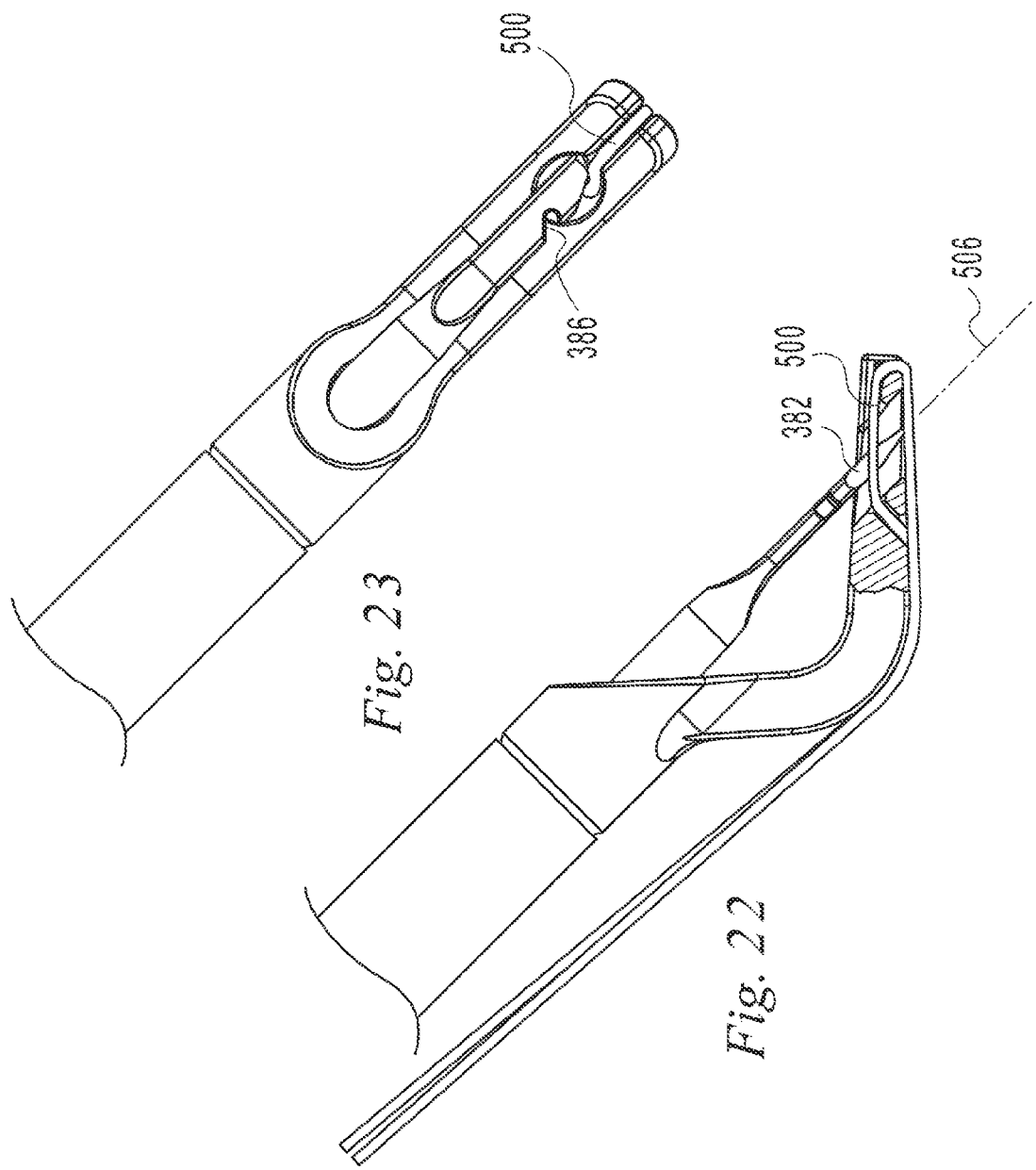

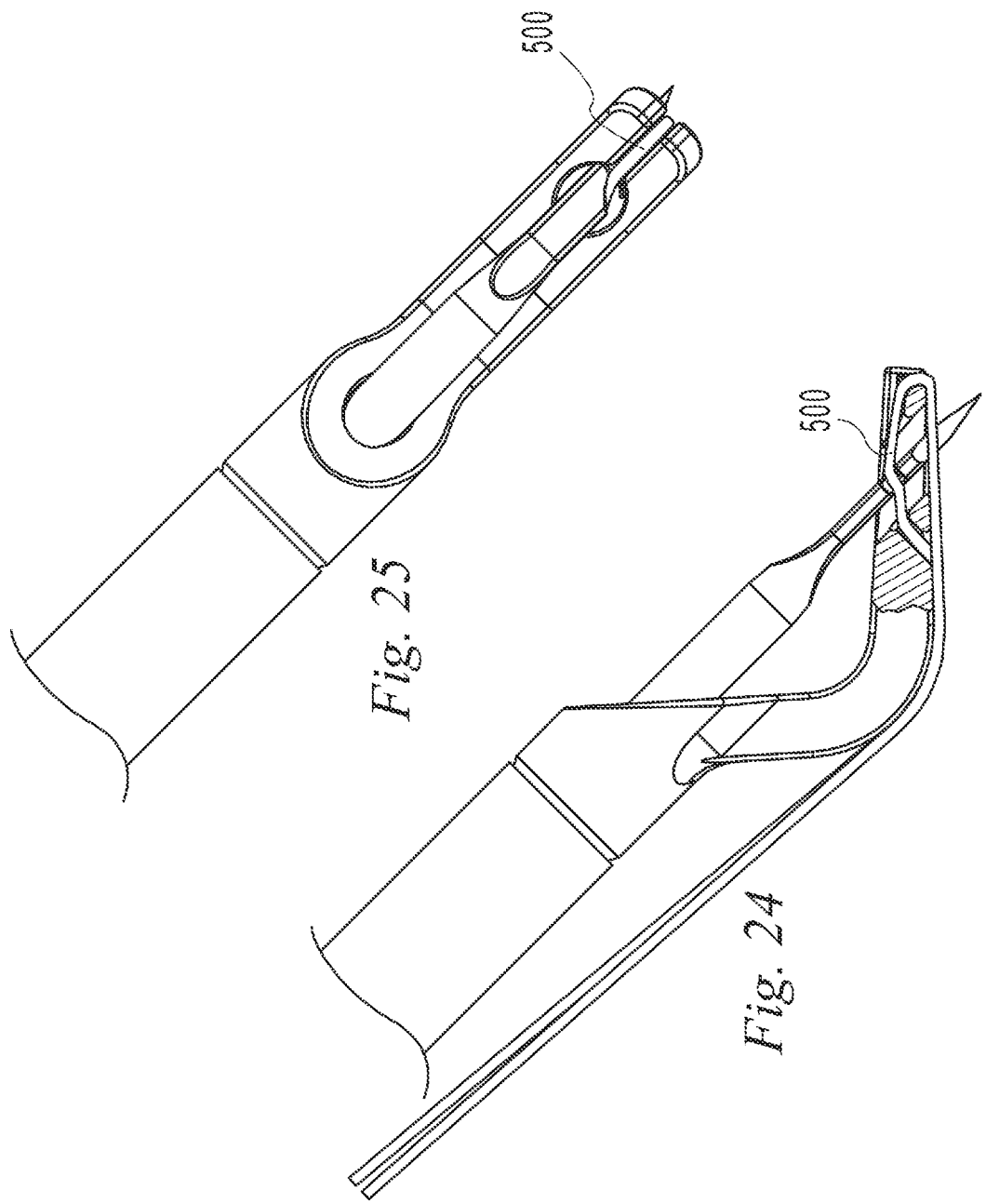

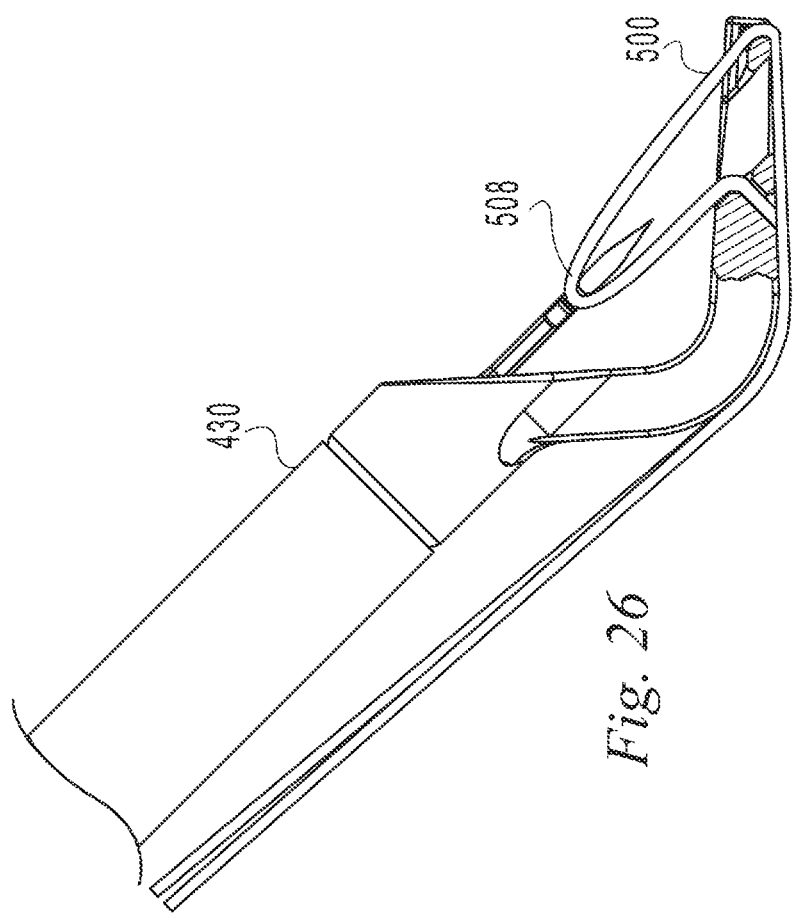

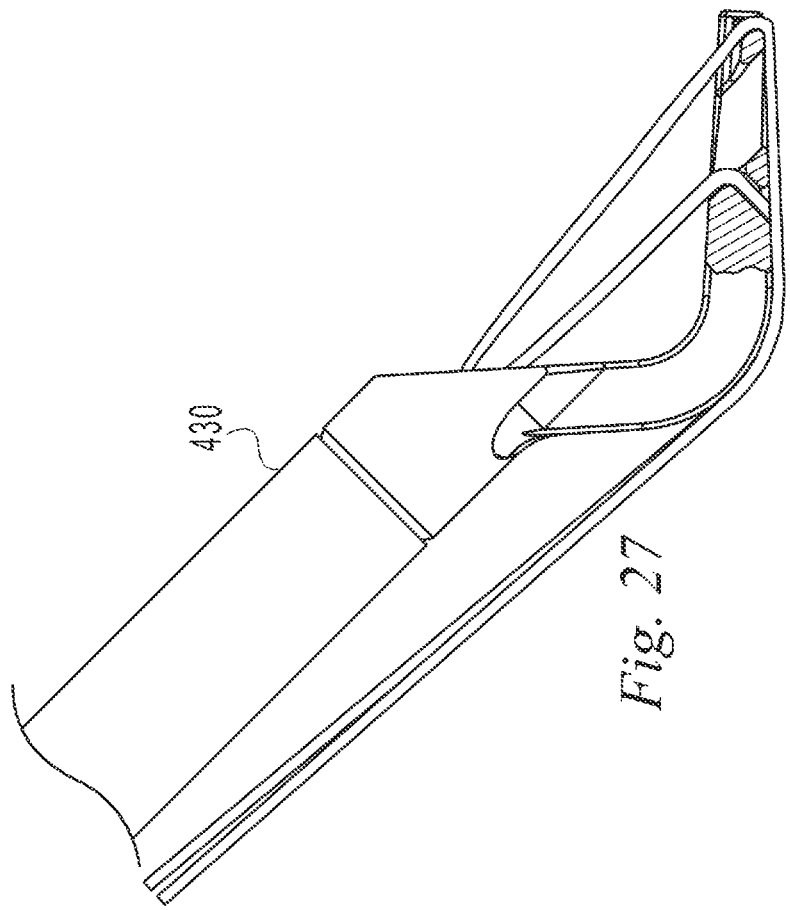

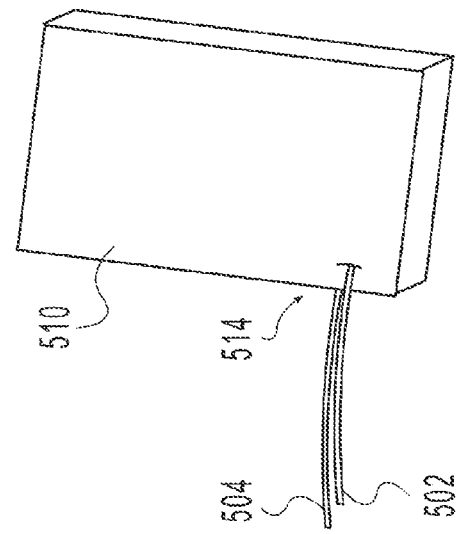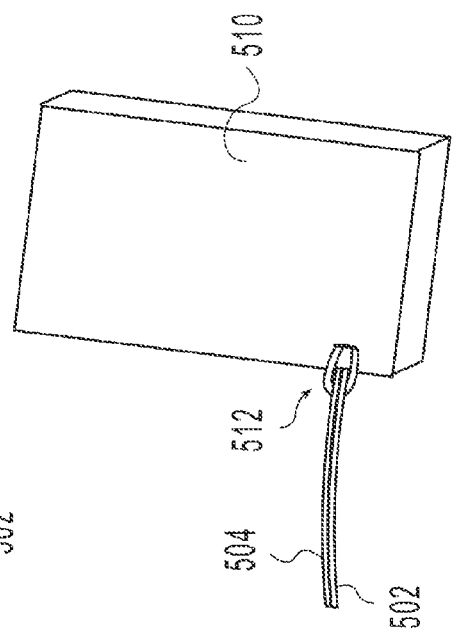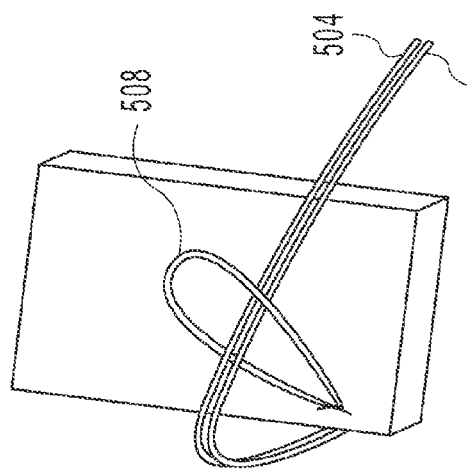

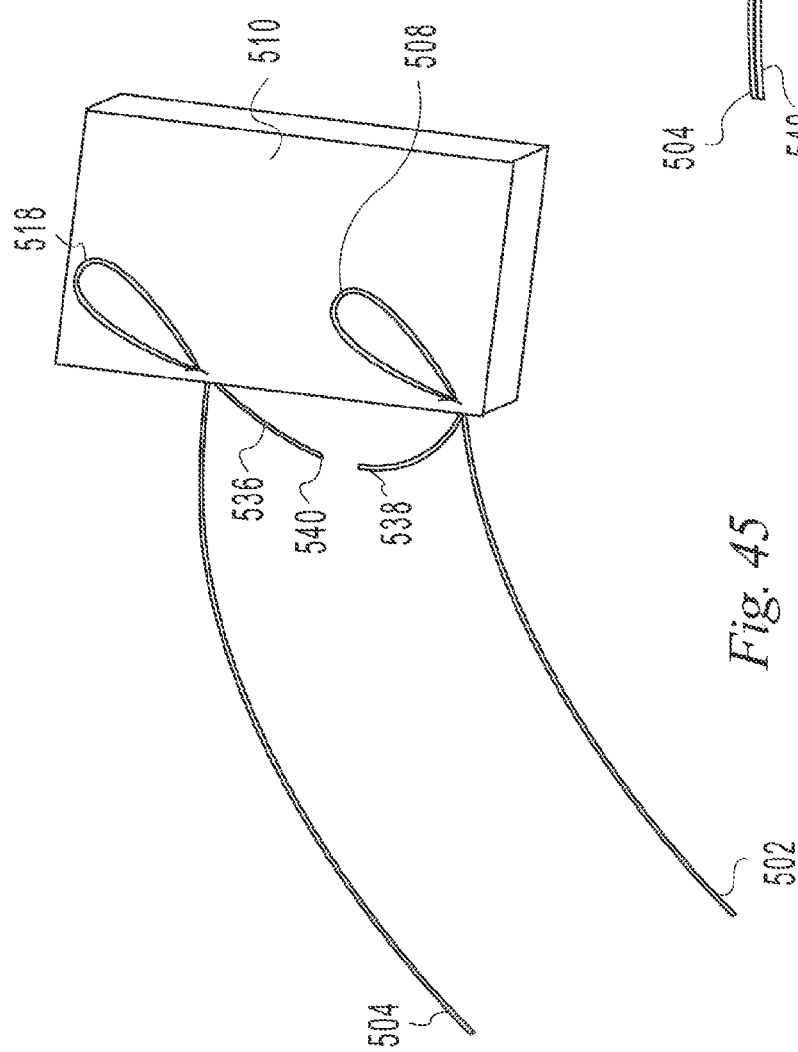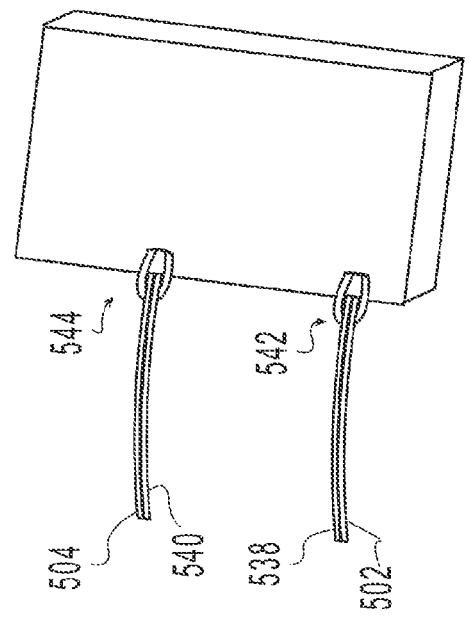

SUTURE PASSER AND METHOD

CROSS-REFERENCE TO RELATED APPLICATIONS

This application claims the benefit of U.S. Provisional Application No. 61/568,137, filed Dec. 7, 2011, U.S. Provisional Application No. 61/505,992, filed Jul. 8, 2011, U.S. Provisional Application No. 61/506,000, filed Jul. 8, 2011, U.S. Provisional Application No. 61/506,004, filed Jul. 8, 2011, all of which are herein incorporated by reference.

FIELD OF THE INVENTION

The invention relates to devices and methods to pass a suture and, in particular, to suturing material such as, for example, soft tissue in reconstructive surgery of a joint such as for example of the foot or hand.

BACKGROUND

Various conditions affecting a patient may require surgical intervention involving passing a suture for example to repair a tear, repair an incision, pass grafts, attach grafts, and anchor implants. Various suture passers have been proposed. There is a need for an improved suture passer able to access confined spaces and able to pass a suture through difficult to penetrate materials such as tough connective tissues.

SUMMARY

The present invention provides a suture passer and method to pass a suture through material during a surgical intervention.

In one aspect of the invention a suture passer includes a housing defining a linear motion axis extending proximally to distally and a needle mounted for translation along the motion axis between a first proximal position and a second distal position. The suture passer may include a foot mounted to the housing and having an opening in a proximal facing surface to receive the needle in the second position.

In another aspect of the invention a suture passer includes a housing, a needle, and a foot and the foot includes a passage from a distal facing surface to an exit adjacent a needle receiving opening. A groove may be formed in a proximally facing surface adjacent the passage and a notch may be formed in the distal end of the foot adjacent the groove such that the passage, groove and notch are able to receive a suture through the distal portion, across the needle receiving opening, along the proximally facing surface, and around the distal end.

In another aspect of the invention, a suture passer includes a housing, a needle mounted for motion between a first position and a second position, and a foot. The foot may position a suture in the path of the needle. The needle may have a notch engageable with the suture in the second position and impart a proximally directed force on the suture as the needle moves toward the first position. The needle may have a shaft with a bevel engageable with the suture to deflect the suture away from the needle axis as the needle is moved toward the second position. The notch may have a width and a depth. The width and depth may be related to the diameter of the suture. The width and depth may be related to the compliance of the suture.

In another aspect of the invention, a method of passing a suture through a material includes positioning a distal portion of a foot of a suture passer behind the material, extending a needle through the material; and retracting the needle to retrieve a bight of suture from the distal portion proximally through the material. The method may include retrieving multiple, connected bights of suture through the material to form a running stitch.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 9 is a perspective view of a component of the suture passer of FIG. 1;

FIG. 10 is a side elevation view of the component of FIG. 9;

FIG. 11 is a bottom plan view of a component of the suture passer of FIG. 1;

FIG. 12 is a side elevation view of the component of FIG. 11;

FIG. 13 is a sectional view taken along line 13-13 of FIG. 12;

FIGS. 14A-G are bottom plan views of variations of the component of FIG. 11;

FIG. 15 is a partially sectioned side elevation view of the distal end of the suture passer of FIG. 1 illustrating a suture being loaded on the suture passer;

FIG. 16 is a top plan view of the distal end of the suture passer of FIG. 1 illustrating a suture being loaded on the suture passer;

FIG. 17 is a partially sectioned side elevation view of the distal end of the suture passer of FIG. 1 illustrating a suture being loaded on the suture passer;

FIG. 18 is a top plan view of the distal end of the suture passer of FIG. 1 illustrating a suture being loaded on the suture passer;

FIG. 19 is a partially sectioned side elevation view of the distal end of the suture passer of FIG. 1 illustrating a suture being loaded on the suture passer;

FIG. 20 is a top plan view of the distal end of the suture passer of FIG. 1 illustrating a suture being loaded on the suture passer;

FIG. 22 is a partially sectioned side elevation view of the distal end of the suture passer of FIG. 1 illustrating the operation of the suture passer;

FIG. 23 is a top plan view of the distal end of the suture passer of FIG. 1 illustrating the operation of the suture passer;

FIG. 24 is a partially sectioned side elevation view of the distal end of the suture passer of FIG. 1 illustrating the operation of the suture passer;

FIG. 25 is a top plan view of the distal end of the suture passer of FIG. 1 illustrating the operation of the suture passer;

FIG. 26 is a partially sectioned side elevation view of the distal end of the suture passer of FIG. 1 illustrating the operation of the suture passer;

FIG. 27 is a partially sectioned side elevation view of the distal end of the suture passer of FIG. 1 illustrating the operation of the suture passer; and FIGS. 28-46 are perspective views illustrating the suture passer of FIG. 1 in use to pass sutures through a material to create a variety of stitches.

DESCRIPTION OF THE ILLUSTRATIVE EXAMPLES

Figure 1:
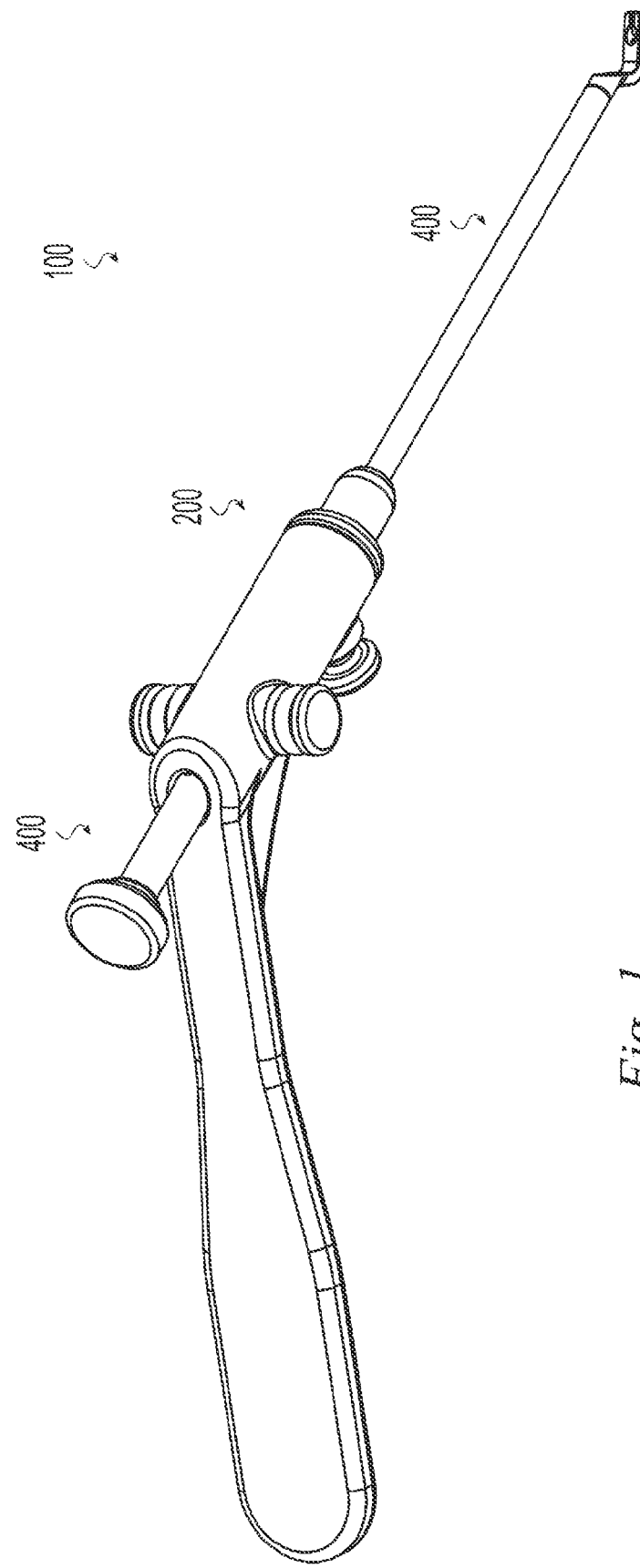
FIG. 1 is a perspective view of an illustrative example of a suture passer according to the present invention.
Figure 2:
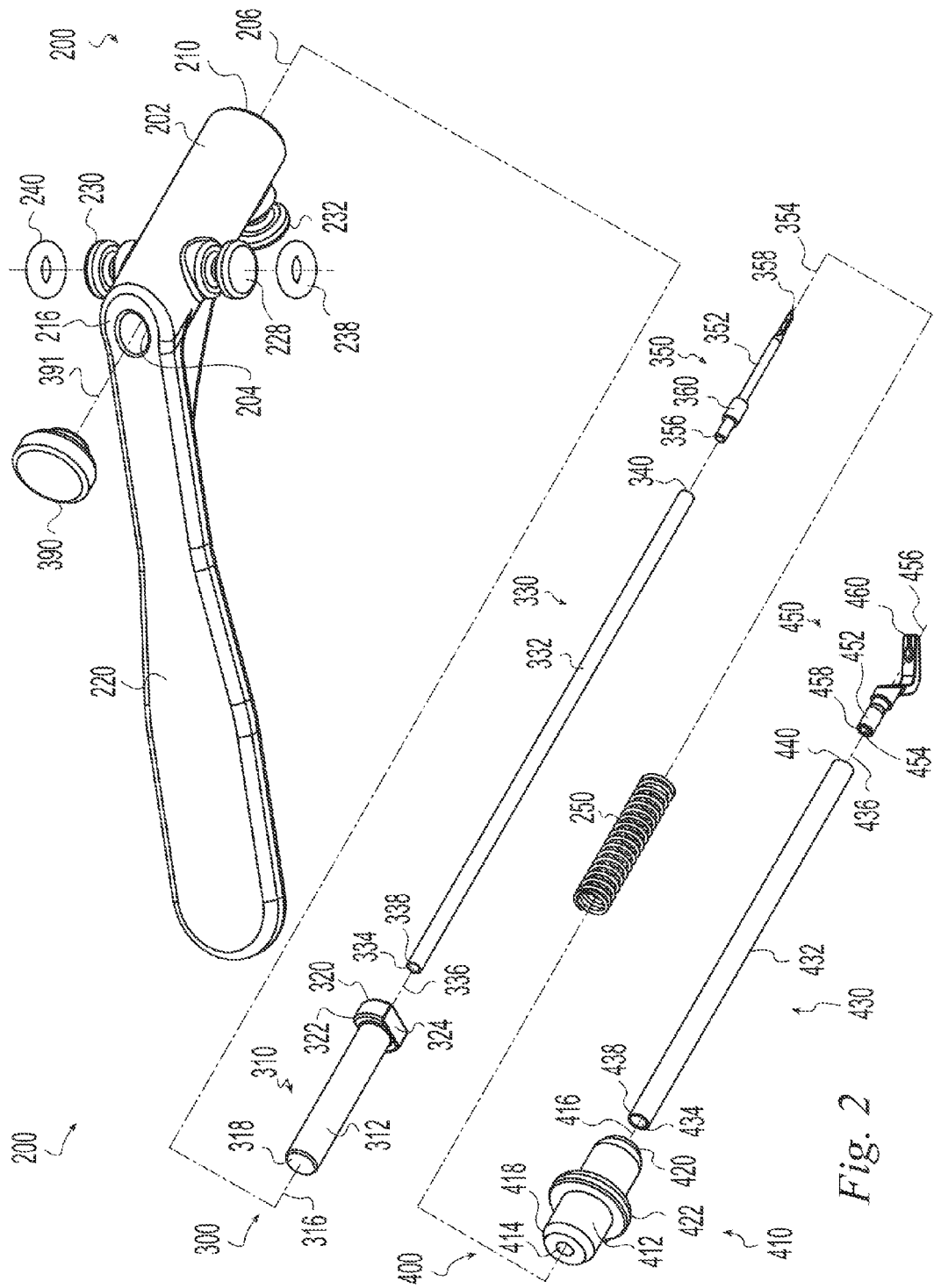
FIG. 2 is an exploded perspective view of the suture passer of FIG. 1.
Figure 4:
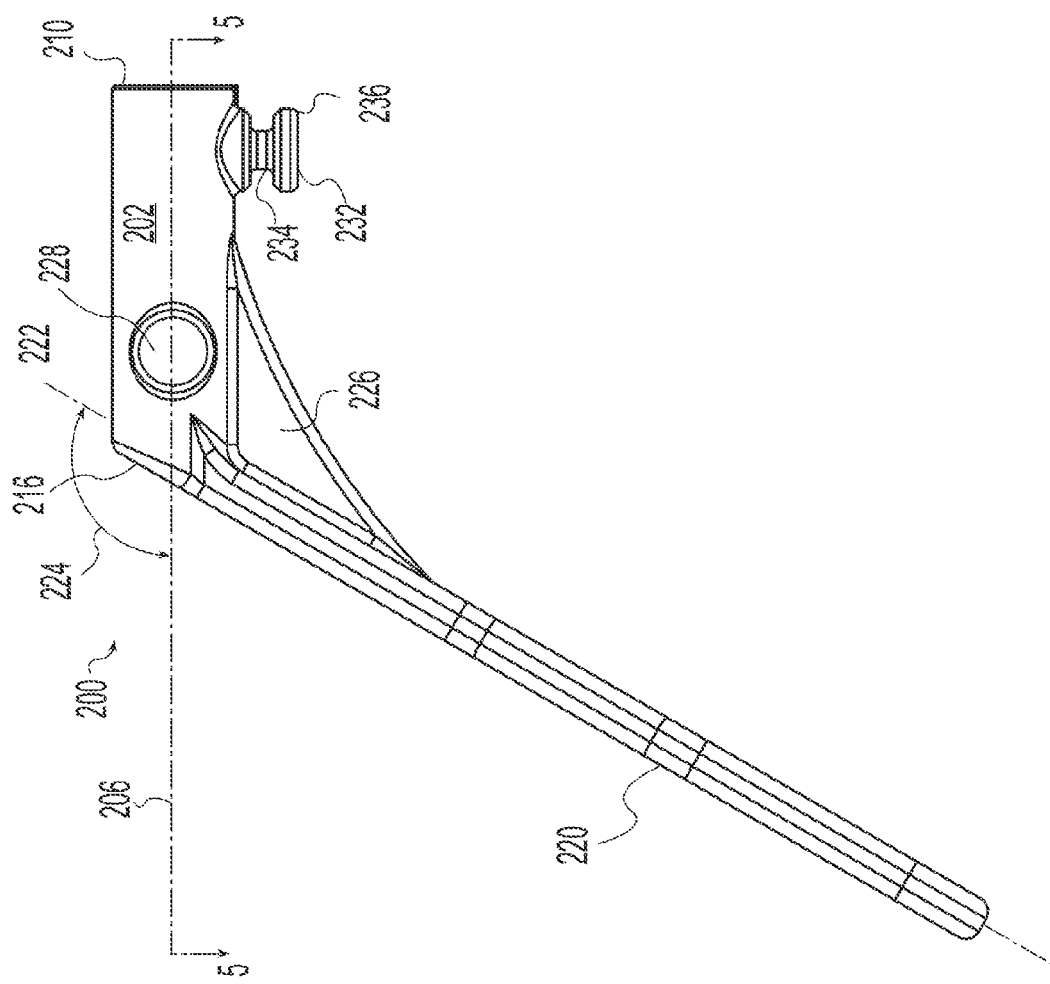
FIG. 4 is a is a side elevation view of the component of FIG. 3.
Figure 3:
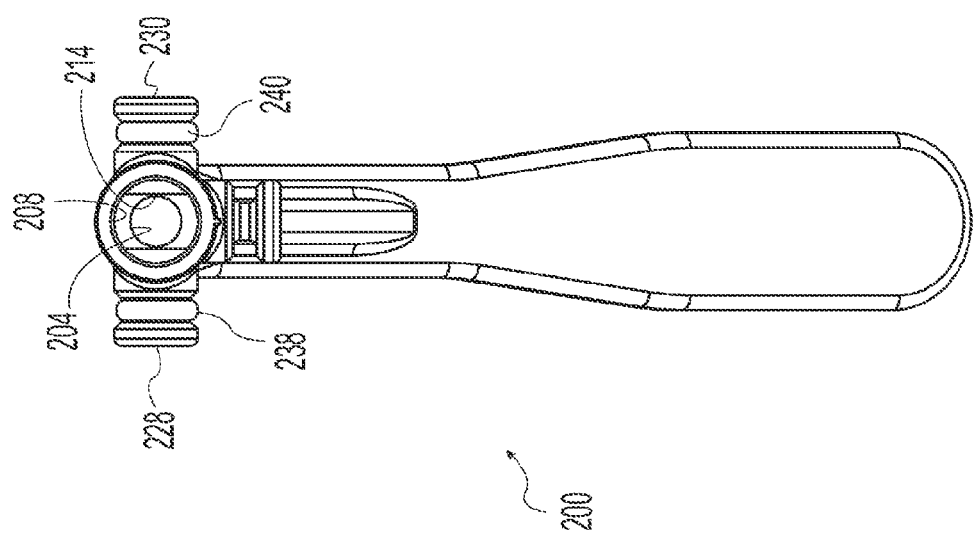
FIG. 3 is a front elevation view of a component of the suture passer of FIG. 1.
Figure 5:
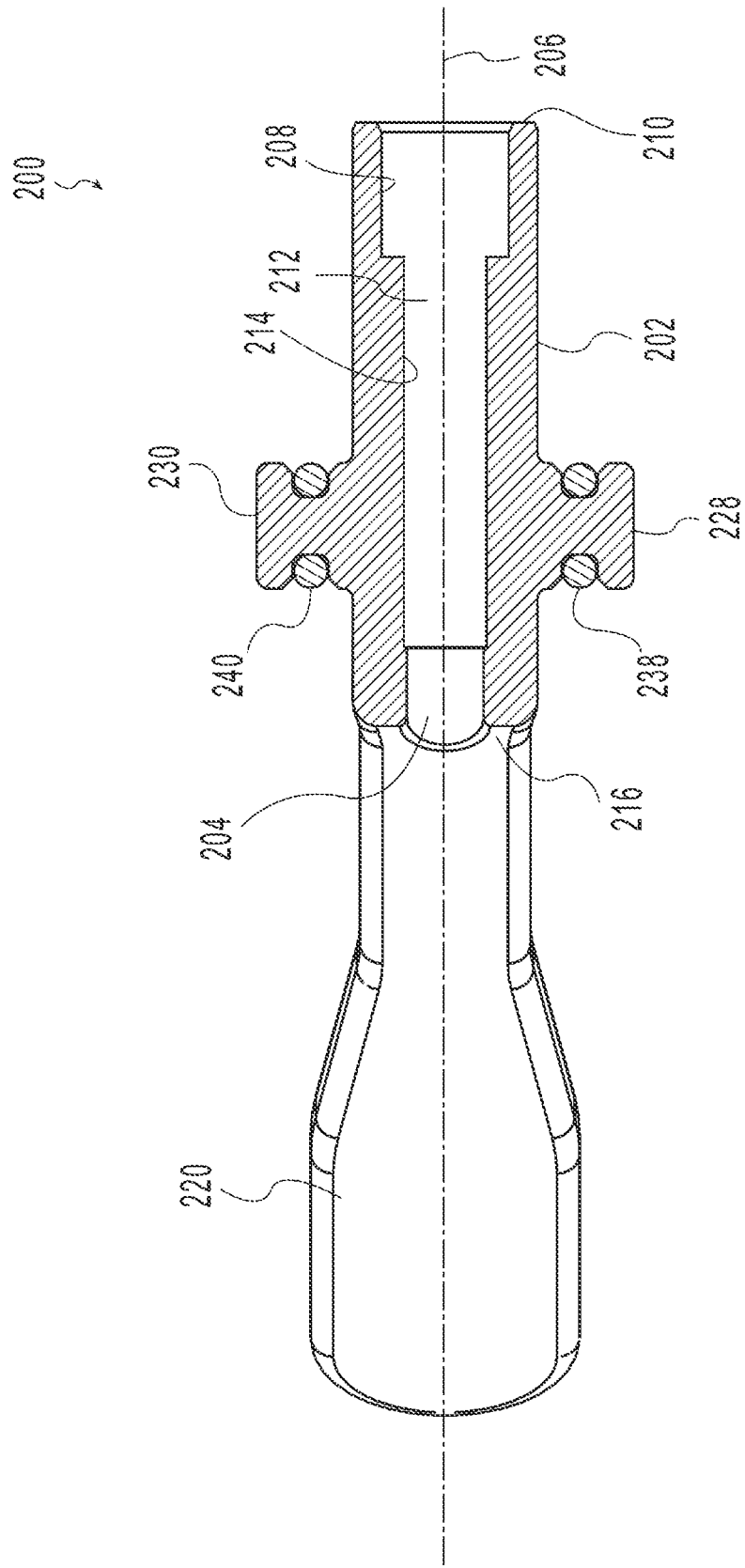
FIG. 5 is a sectional view taken along line 5-5 of FIG. 4.
Figure 6:
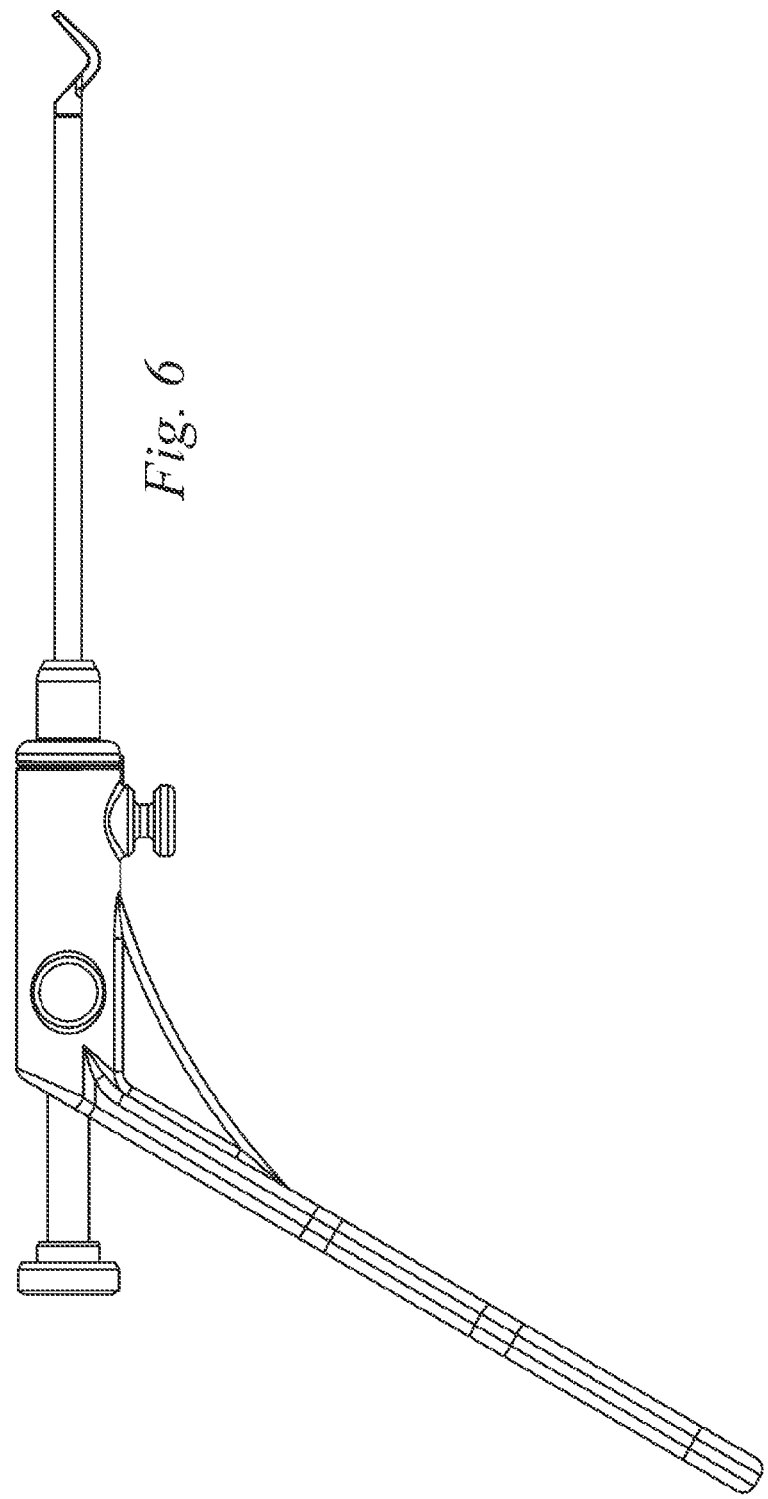
FIG. 6 is a side elevation view of the suture passer of FIG. 1.
Figure 7:
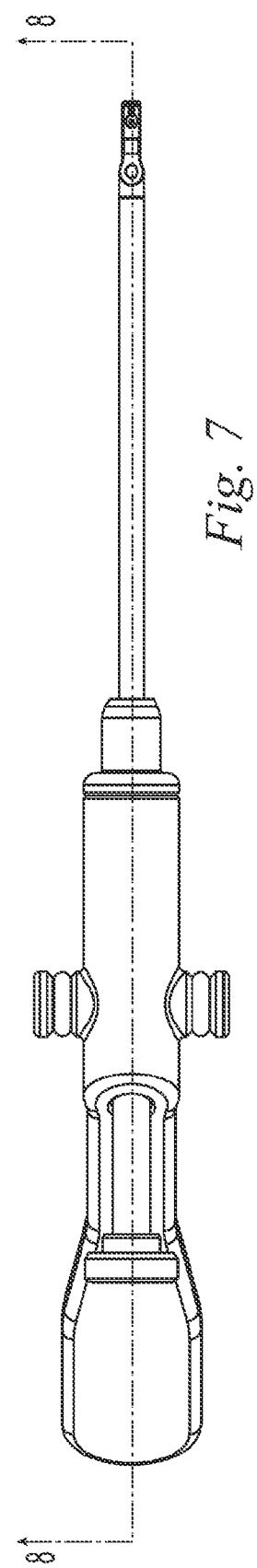
FIG. 7 is a top plan view of the suture passer of FIG. 1.
Figure 8:
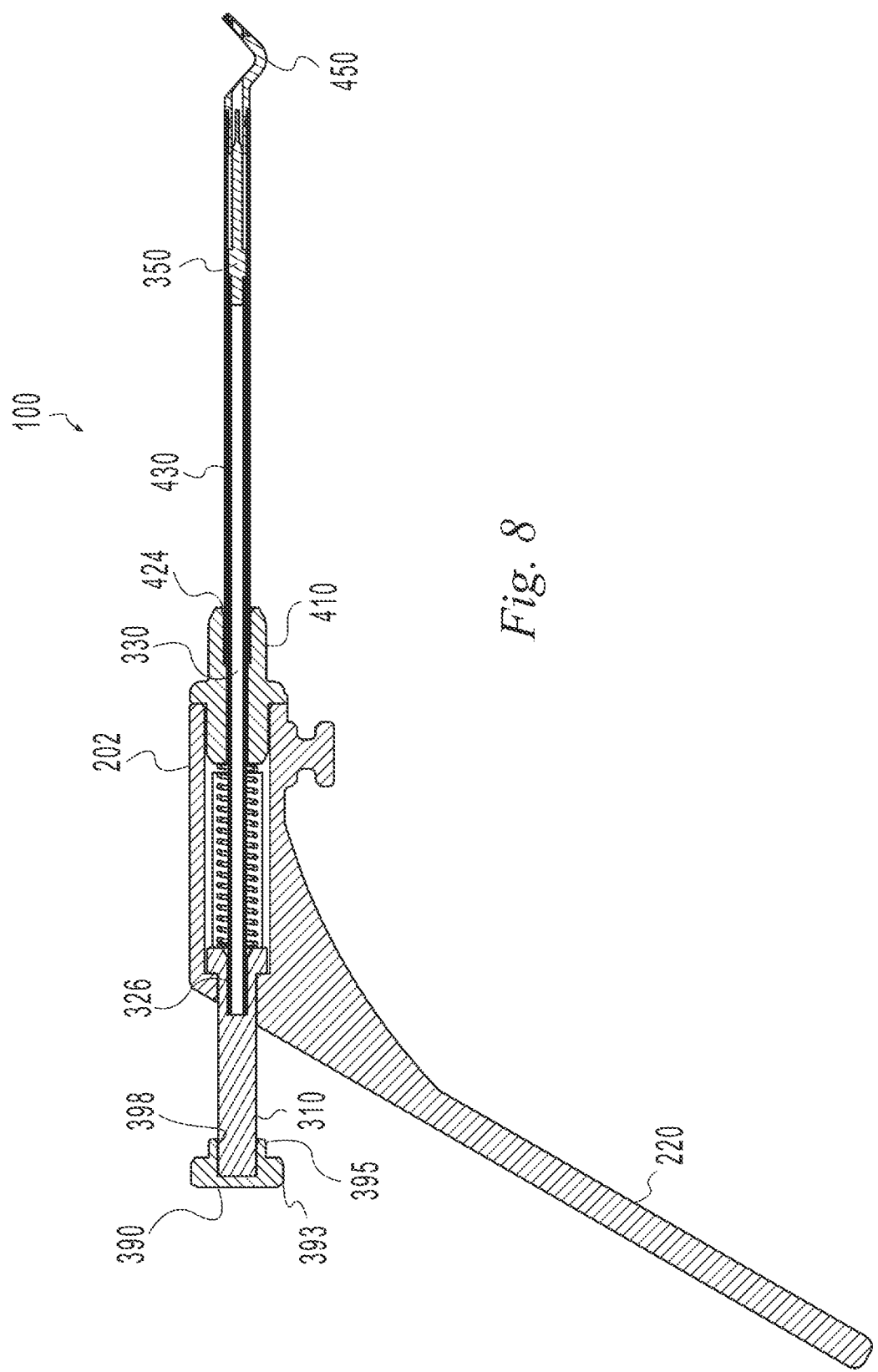
FIG. 8 is a sectional view taken along line 8-8 of FIG. 7.
Figure 14A:
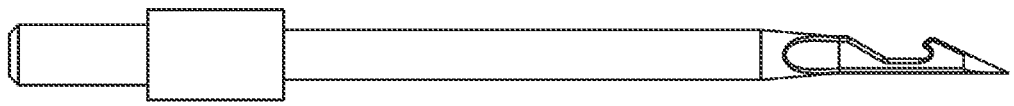
Figure 14B:
Figure 14C:
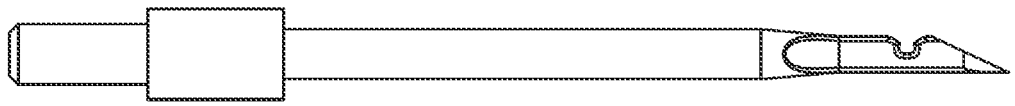
Figure 4D:
Figure 14E:
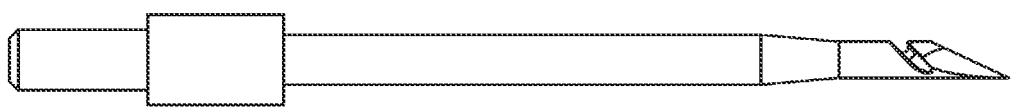
Figure 14F:
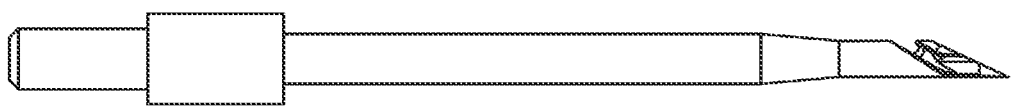
Figure 14G:
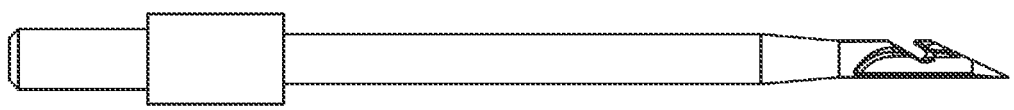

The following illustrative examples depict instruments and techniques to pass a suture through a material. Instruments and techniques according to the present invention may be used to pass a suture through any material, at surgical sites anywhere in a patient's body, and for any purpose. Instruments and techniques according to the present invention are particularly useful where access to confined spaces and the ability to pass a suture through difficult to penetrate materials are needed. For example, surgery on the hands and feet often involve working in confined spaces around small joints and tough connective tissues through which it may be desirable to pass a suture. The terms "suture" and "suture strand" are used herein to mean any strand or flexible member, natural or synthetic, able to be passed through material and useful in a surgical procedure. The term "material" is used herein to mean implants, grafts, fabric, tendon, ligament, fascia, skin, muscle, bone, and any other material through which it is desirable to pass a suture. The term "transverse" is used herein to mean crossing as in non-parallel. The term "bight" is used herein to mean a bend or loop formed in the intermediate portion of a suture.

FIGS. 1-13 depict an illustrative example of a suture passer 100. The suture passer 100 includes a housing 200, a needle assembly 300, and a barrel assembly 400 mounted together and operable to translate the needle assembly 400 between a first, retracted position and a second, extended position to manipulate a suture strand.

The housing 200 includes a hollow receiver portion 202 having a hollow through bore 204 with a longitudinal bore axis 206. An enlarged counter bore 208 is formed coaxial with the through bore 204 at a distal end 210 of the receiver 202. An intermediate portion 212 of the through bore 204 has flat side walls 214. A handle 220 extends downwardly and proximally from the receiver 202 and has a longitudinal handle axis 222. The handle axis 222 forms an angle 224 with the bore axis 206. The angle 224 is in the range of 90 to 180 degrees; preferably 100 to 140 degrees; more preferably 110 to 130 degrees. In the illustrative example of FIGS. 1-3, the angle 224 is 120 degrees. A gusset 226 extends between the handle 220 and the receiver 202 for strength. One or more knobs extend from the housing to provide suture strand anchor or routing points. In the illustrative example of FIGS. 1-3, first and second opposed side knobs 228, 230 and a downwardly projecting bottom knob 232 are mounted to the receiver 202. Each knob has a narrow waist 234 and an enlarged head 236 as shown with reference to the bottom knob 232. A suture strand may be wrapped or tied around the waist 234 to secure or route the suture. O-rings 238, 240 are provided on the side knobs 228, 230 to grip a wrapped suture to facilitate securing and removing a suture strand. As a suture is wrapped around the side knobs 228, 230, it wedges between the resilient O-ring 238, 240 and knob compressing the O-ring. The pressure of the O-ring pressing the suture strand against the knob as well as the deformation of the O-ring around the suture strand temporarily secures the suture.

The needle assembly 300 includes a piston 310, a stem 330, a needle 350, and a button 390. The piston 310 has a generally cylindrical body 312 with a longitudinal axis 316 extending from a proximal end 318 to a distal end 320. A flange 322 extends radially outwardly from the body 312 near the distal end 320. The flange has opposed flattened sides 324. A bore 326 (FIG. 8) is formed coaxially in the piston 310 at the distal end of the body 312. The stem 330 includes an elongated hollow cylinder 332 having an outer diameter and an inner bore 334 defining a longitudinal axis 336 extending from a proximal end 338 to a distal end 340. The needle 350 is a generally cylindrical member having a shank 352 with an outer diameter defining a longitudinal axis 354 extending from a proximal end 356 to a distal tip 358. A flange 360 extends radially outwardly from the shank 352 at a position intermediate the proximal and distal ends. The needle 350 will be described in greater detail below. The button 390 has a generally cylindrical body with a longitudinal axis 391 extending from a proximal end 393 to a distal end 395. A bore 398 (FIG. 8) is formed coaxially in the button 390 at the distal end 395 of the body. The proximal portion of the needle shank 352 fits within the inner bore 334 of the stem at its distal end 340. The stem outer diameter, near its proximal end 338, fits within the bore 326 of the piston 310. The outer diameter of the piston 310 fits within the bore 204 of the receiver 202 in linear sliding relationship. The flat sides 324 of the piston engage the flat side walls 214 of the bore 204 to prevent the needle assembly from rotating relative to the receiver 202. The piston flange 322 abuts the proximal end of the intermediate portion 212 of the bore 204 of the receiver 202 to provide a stop to needle assembly proximal translation relative to the receiver 202. The outer diameter of the piston 310, near its proximal end, fits within the bore 398 of the button 390 and the button 390 abuts a proximal end 216 of the receiver to provide a stop to needle assembly distal translation relative to the receiver 202. The joints between the button 390 and piston 310, the piston 310 and the stem 330, and stem 330 and needle 350 are secured by pressing, gluing, pinning, welding, or other suitable securing means. Alternatively, two or more of these components or various combinations of them may be made as a single piece.

The barrel assembly 400 includes a barrel bushing 410, a barrel 430, and a foot 450. The bushing 410 has a generally cylindrical body 412 having a through bore 414 with a longitudinal axis 416 extending from a proximal end 418 to a distal end 420. A flange 422 extends radially outwardly from the body 412 at a position intermediate the proximal and distal ends. An enlarged counter bore 424 (FIG. 8) is formed coaxial with the through bore 414 at the distal end 420 of the body 412. The barrel 430 includes an elongated hollow cylinder 432 having an outer diameter and an inner bore 434 defining a longitudinal axis 436 extending from a proximal end 438 to a distal end 440. The foot 450 is a generally hook-shaped member having a hollow post 452 having an outer diameter and an inner bore 454 defining a longitudinal axis 456 extending from a proximal end 458 of the cylinder to a distal end 460 of the foot 450. The foot will be described in greater detail below. The foot post 452 outer diameter fits within the inner bore 434 of the barrel at its distal end 440. The barrel 430 outer diameter, near its proximal end 438, fits within the counter bore 424 of the bushing. A coiled compression spring 250 fits coaxially over the needle assembly 300 within the bore 204 of the receiver 202 and rests against the distal end of the piston flange 322. The barrel assembly 400 fits coaxially over the needle assembly 300 and the outer diameter of the bushing 410, near its proximal end 418, fits within the counter bore 208 of the receiver 202 and is pressed proximally until the flange 422 abuts the receiver distal end 210. The proximal end of the bushing retains the spring 250 within the bore 204. The joints between the foot 450 and barrel 430, the barrel 430 and bushing 410, and the bushing 410 and receiver 202 are secured by pressing, gluing, pinning, welding, or other suitable securing means. Alternatively, the bushing, barrel, foot, or any combination of them may be made as a single piece. Pressing the button 390 distally translates the needle assembly from a first, proximal, retracted position distally along the needle axis 354 compressing the spring 250 and extending the needle 350 through the foot 450 to a second, distal, extended position. Releasing the button 390 allows the spring 250 to expand and bias the needle assembly 300 back toward the first position. The needle assembly 300 of the illustrative example of FIGS. 1-13 is a linear arrangement mounted for linear, coaxial translation in the housing 200 and barrel assembly 400 with the needle projecting straight through the foot to increase rigidity and power facilitating driving the needle 350 through difficult to penetrate materials and access confined spaces. The barrel 430 may have a circular, polygonal, or any other cross sectional shape.

FIGS. 9 and 10 illustrate the foot 450 of the illustrative example of FIGS. 1-13 in greater detail. The hooked portion of the foot 450 includes an elbow 462 having a first, proximal portion 464 extending distally from the post 452 along a proximal portion axis 465 diverging from the bore axis 456 at a first angle 466 relative to the bore axis 456. A second, distal portion 468 extends distally from the first portion 464 along a distal portion axis 469 converging toward the bore axis 456 at a second angle 470 relative to the bore axis 456. The first and second angles 466, 470 are chosen to allow the foot to extend into a confined space, for example behind material such as a portion of soft tissue such as a tendon or ligament, and position the receiver 202 so as not to obstruct the users view of the foot and needle. The first angle 466 is in the range of 0 to 180 degrees; preferably 0 to 90 degrees; more preferably 25 to 55 degrees; more preferably 35 to 45 degrees. In the illustrative example of FIG. 10, the first angle 466 is approximately 42 degrees. The second angle 470 is in the range of 0 to 90 degrees; preferably 25 to 55 degrees; more preferably 35 to 45 degrees. In the illustrative example of FIGS. 9 and 10, the second angle 470 is also approximately 42 degrees. An eye 472 is formed through the second portion 468, from a proximal facing surface 474 to a distal facing surface 476, coaxial with the bore axis 456 for receiving the distal end of the needle 350 when the needle is in the second position. A hole 478 defining a hole axis 480 extends through the second portion 468 from the distal surface 476 and intersecting the eye 472. The hole 478 permits passing a suture strand from the distal surface 476 of the second portion 468 to the eye 472. The hole axis 480 forms an angle 482 relative to the bore axis 456. The angle 482 is between parallel to the proximal facing surface 474 of the second portion 468 and parallel to the distal facing surface of the first portion 464; preferably in the range of 45 to 135 degrees; more preferably 45 to 90 degrees. In the illustrative example of FIGS. 9 and 10, the hole angle 482 is approximately 90 degrees relative to the bore axis 456. A groove 484 is formed in the proximal surface 474 of the second portion 468 communicating from the eye 472 to the distal end 460. A notch 486 is formed through the distal end 460 from the proximal surface 474 to the distal surface 476 and communicating with the groove 484. The groove 484 and notch 486 are sized to receive a suture strand and retain the strand on the distal end of the foot 450. The proximal surface 474 of the second portion 468 of the foot 450 provides a supporting platform for material through which the needle 350 is passed. The eye 472 allows the needle 350 to penetrate all the way through the material and intercept a suture strand extending from the hole 478 to the groove 484.

FIGS. 11-13 illustrate the needle 350 of the illustrative example of FIGS. 1-13 in greater detail. A narrowed shaft 362 extends between the shank 352 and a sharp tip 364 at the distal end of the needle. A shoulder 366 defines the transition from the shank 352 to the shaft 362. The shaft 362 is generally rectangular in cross section with a top 368, a bottom 370, and opposing sides 372, 374. The corners 376 are rounded. The shaft 362 has a height 378 between the top 368 and bottom 370 and a width 380 between the sides 372, 374. Both the height 378 and width 380 of the shaft are narrower than the shank 352. The width 380 of the shaft 362 is greater than its height 378. The ratio of the width 380 to the height 378 is in the range of 1 to 3; preferably 2 to 3. In the illustrative example of FIGS. 11-13 the ratio is approximately 2.3. The distal end of the shaft is tapered in the width dimension from the full width to the tip 364. In the illustrative example of FIGS. 11-13, the shaft is tapered on a single side in the width dimension to form a single-sided bevel 382. The distal end of the shaft is tapered in the height dimension from the full height to the tip 364. In the illustrative example of FIGS. 11-13, the shaft is tapered on opposite sides in the height dimension to form a chisel portion 384. A notch 386 is formed in the side of the shaft 362 through the shaft 362 from the top 368 to the bottom 370. The notch 386 has an opening width 388 measured parallel to the needle axis 354, a depth 389 measured perpendicular to the needle axis 354, and a notch axis 392 forming an angle 394 to the needle axis 354. In the illustrative example of FIGS. 22-13, the notch has parallel side walls 396, 398 that are parallel to the axis 392. The notch width 388, depth 389, and angle 394 are selected to optimize the ability of the needle 350 to capture and retain a suture strand while avoiding snagging other material through which the needle 350 passes. FIGS. 14A-14G illustrate a variety of needle designs having varying notch width, depth, and angle. The present inventors have determined that the balance between capturing and retaining a suture strand and avoiding snagging is optimized, in the case of a suture strand with a diameter D, when the width of the notch is in the range of 0.9 D to 2 D. A notch width of 0.9 D creates a press fit depending on the resilient nature of the suture strand. Preferably, the notch width is in the range of 1 D to 1.5 D. Similarly, the notch depth is optimized when the depth is in the range of 0.75 D to 3 D. A notch depth of 0.75 D captures the suture but leaves a portion of the suture projecting from the notch. Preferably, the depth is in the range of 1 D to 2 D. The notch angle is in the range of 30 to 90 degrees; preferably 35 to 55 degrees. In the illustrative example of FIGS. 11-13, the notch was optimized for a USP#2-0 suture having a diameter in the range of 0.300-0.339 mm and has a width of 0.30 mm and a depth of 0.46 mm and an angle of 45 degrees. The notch opens toward the side of the needle 350 and suture passer 100. The bevel 382 leads from the tip 364 of the needle along the narrow side of the needle shaft 362 toward the opening of the notch 386. The needle may be sized to capture and pass one or more suture strands.

Figure 21:
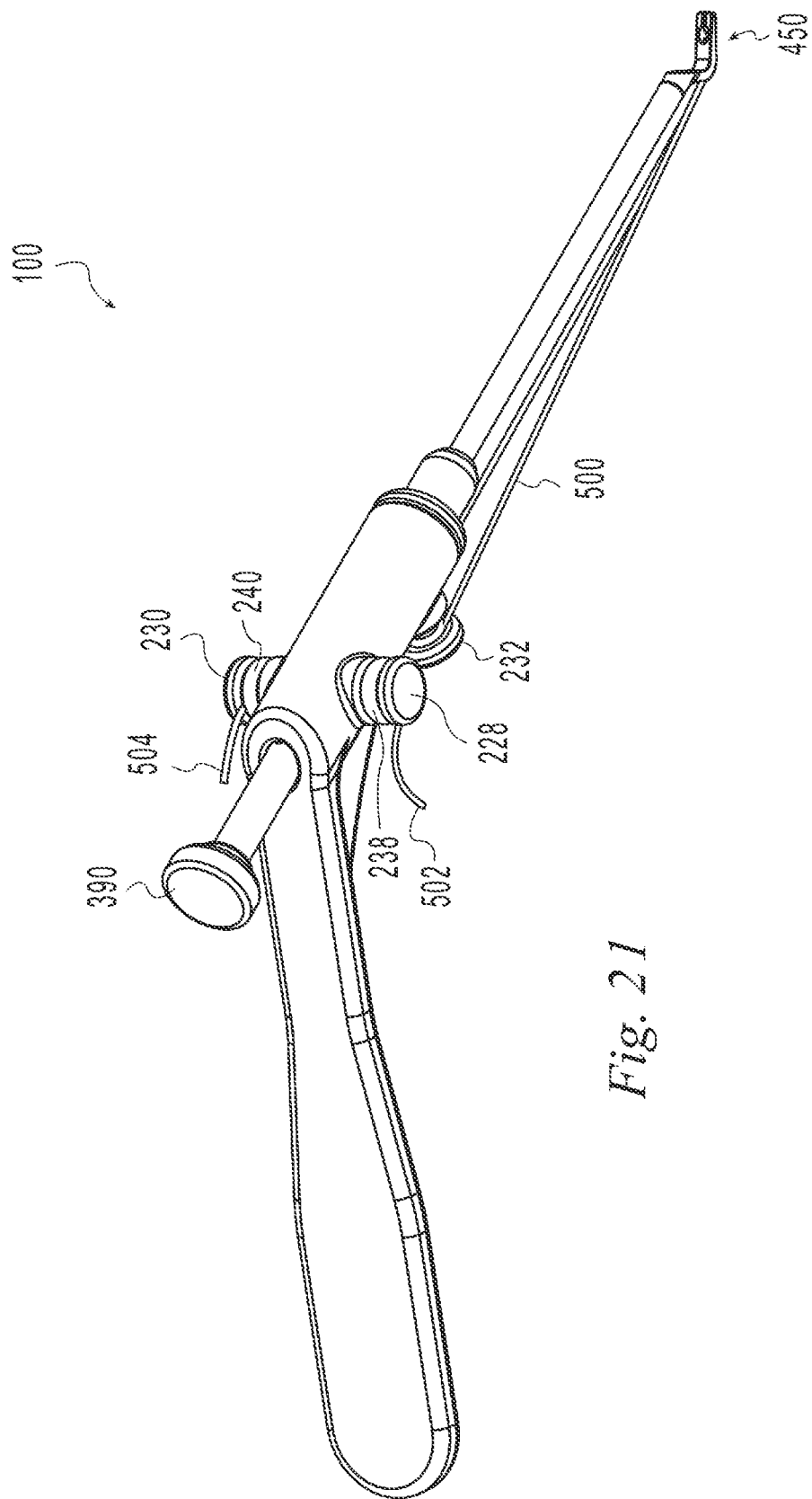
FIG. 21 is a perspective view of the suture passer of FIG. 1 illustrating a suture being loaded on the suture passer.

FIGS. 15-21 illustrate loading a suture strand 500, having a first end 502 and a second end 504 into the suture passer 100 of FIGS. 1-13. A first end 502 of the suture strand 500 is inserted through the hole 478 in the foot 450 from the distal surface 476 toward the eye 472 and extended past the proximal surface 474 as shown in FIGS. 15 and 16. The first end 502 of the suture strand is pulled distally to place the suture strand 500 in the groove 484 as shown in FIGS. 17 and 18. The suture strand 500 is wrapped over the distal end 460 in the notch 486 and pulled proximally over the distal surface 476 of the second portion of the foot 450 as shown in FIGS. 19 and 20. The ends 502, 504 of the suture strand are wrapped around the side knobs 228 and 230 and retained by the O-rings 238, 240. In the example of FIG. 21, the suture strand ends are routed proximally to the bottom knob 232 wrapped part-way around the proximal side of the knob 232 and secured on the side knob opposite the side on which the end was routed such that the suture strand is maintained near the center of the suture passer 100 and better retained on the foot 450.

FIGS. 22-27 illustrate the operation of the suture passer 100. When the button 390 is pressed distally, the needle assembly 300 moves distally relative to the housing and barrel assembly along the straight-line motion axis 506 of the suture passer which is coaxial with the needle axis 354 and foot bore axis 456. As the needle 350 approaches the suture strand 500, the bevel 382 contacts the suture strand 500 and wedges it sideways increasing the tension in the suture as shown in FIGS. 22 and 23. Further advancement of the needle 350 moves the notch 386 toward alignment with the suture strand 500 until the tension in the suture causes the suture 500 to move into the notch 386 as shown in FIGS. 24 and 25. Releasing pressure on button 390 allows the spring 250 to bias the needle assembly proximally. Depending on the resilience of the suture 500 and how tightly it is secured to the knobs 228, 230, the needle may or may not be able to retract. By releasing one or both ends 502, 504 of the suture 500, the suture ends can move toward the foot 450 and allow the needle to retract and pull a bight 508 of suture 500 proximally toward the barrel 430 as shown in FIG. 26. Further retraction of the needle 350 pulls the bight 508 into the barrel 430 (FIG. 27) trapping the bight 508 between the needle 350 and barrel bore 434. To release the bight 508, the button 390 is pressed to advance the needle 350 out of the barrel 430.

Figure 28:
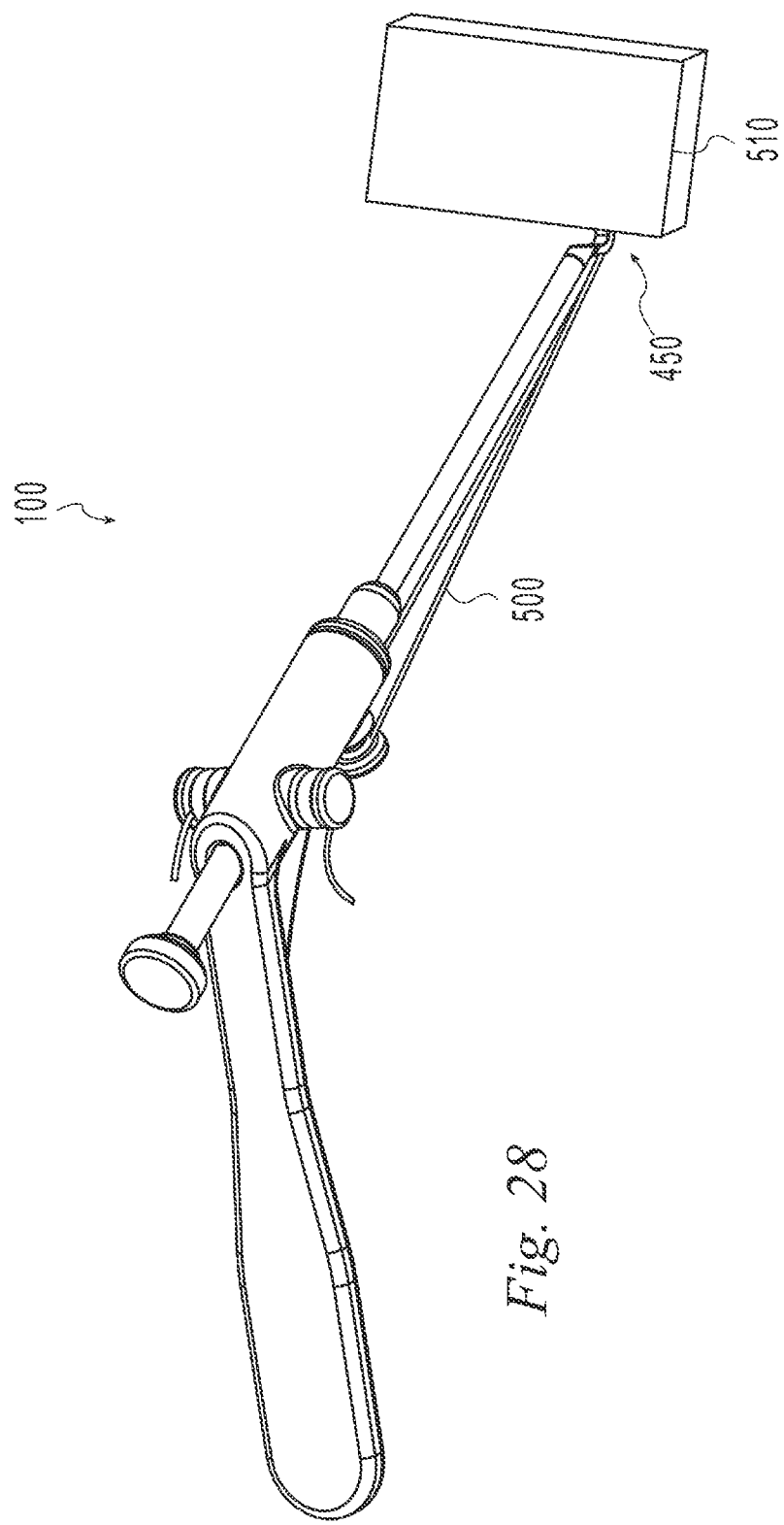
Figure 29:
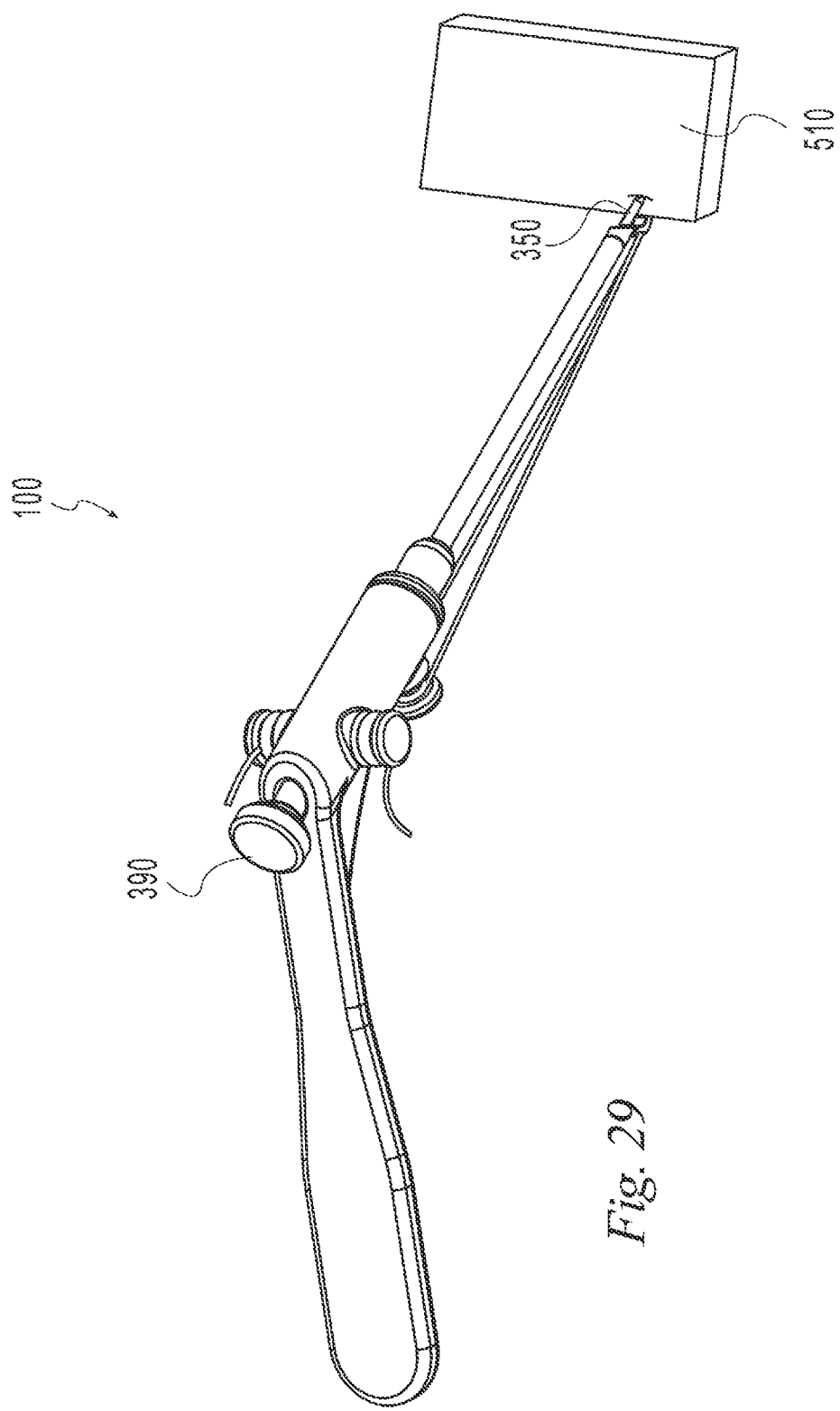
Figure 30:
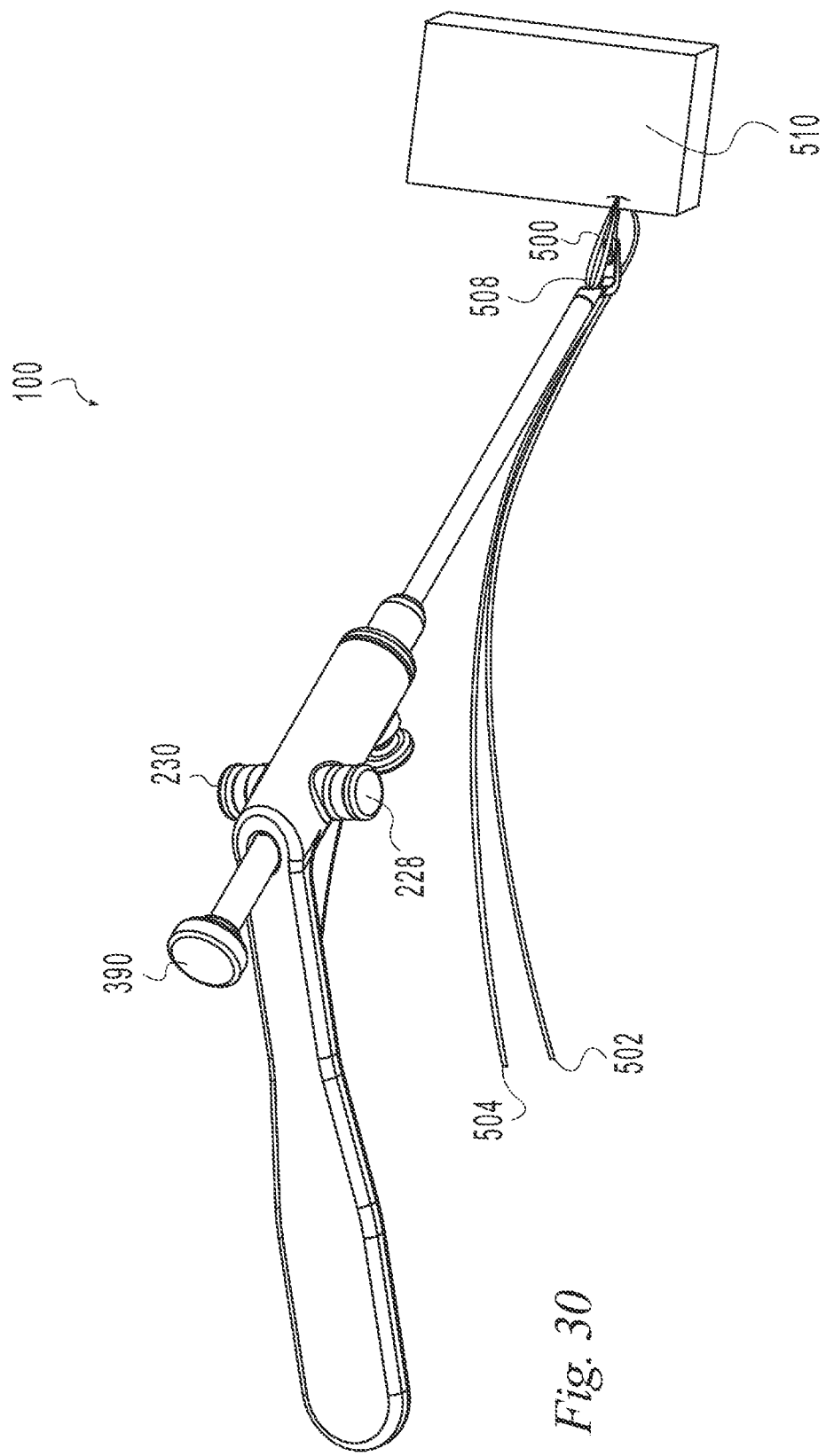
Figure 31:
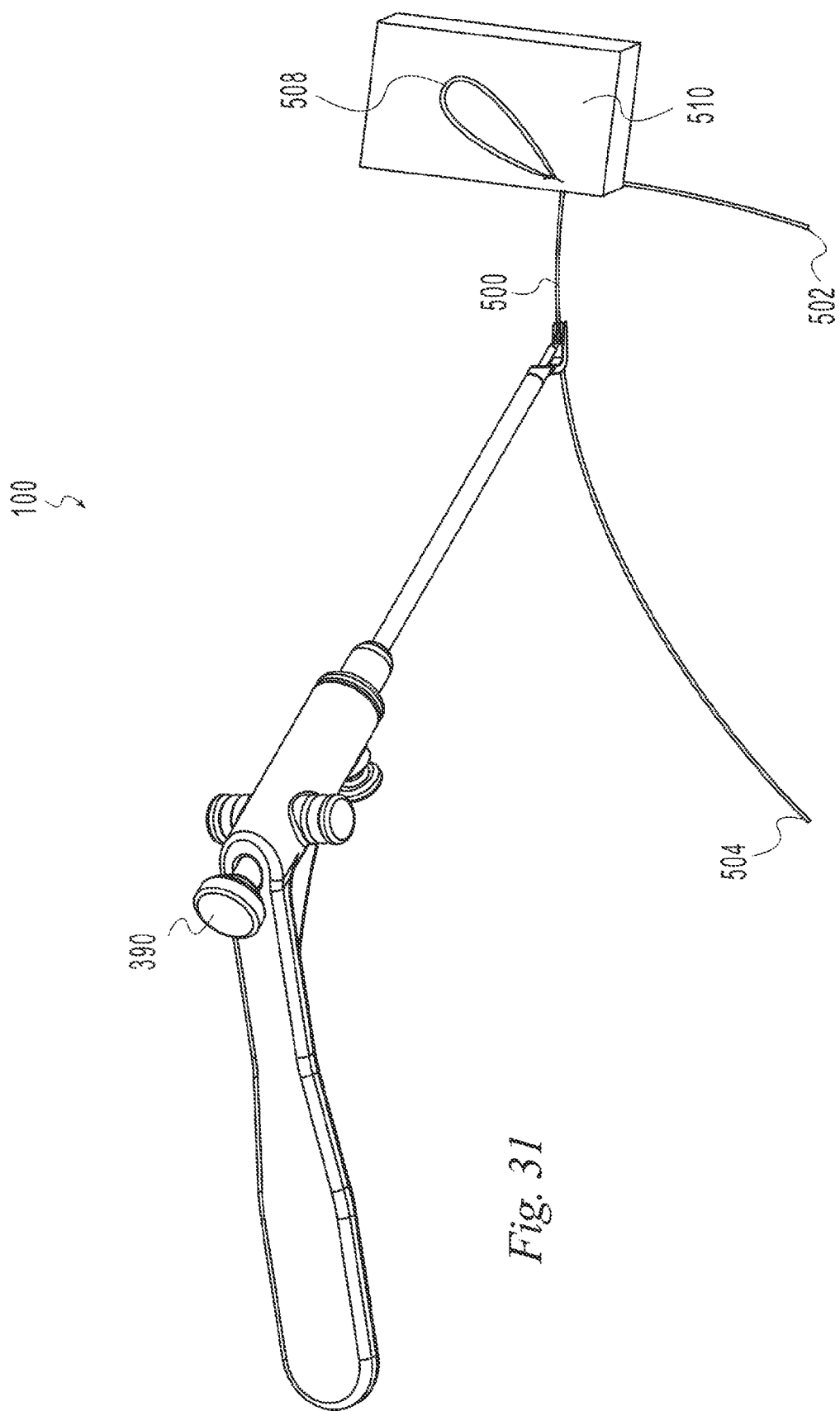

FIGS. 28-46 depict examples of the illustrative suture passer 100 in use to pass sutures through a material to create a variety of stitches. Referring to FIG. 28, the suture passer has been loaded as described relative to FIGS. 15-21. The foot 450 is positioned adjacent material 510 through which it is desired to pass the suture 500. The second portion 468 of the foot is positioned behind the material 510 with the proximal surface 474 supporting the material 510. Referring to FIG. 29, the button 390 is pressed to advance the needle 350 through the material 510 and capture the suture 500 in the eye 472 of the foot 450. Referring to FIG. 30, the button 390 has been released and the suture ends 502 and 504 have been freed from the knobs 228, 230 and allowed to move distally so that the needle 350 has retracted and pulled a bight 508 of suture 500 through the material 510. Referring to FIG. 31, the button 390 has been pressed to release the bight 508 and the first end 502 has been allowed to drop free from the passer 100. Referring to FIGS. 32 and 33, the second end 504 has been removed from the foot 450 by pulling the passer 100 proximally away from the bight or by pulling the suture 500 distally away from the foot 450. The suture ends 502, 504 have been passed through the bight 508 and pulled to form a stitch in the form of a hitch 512.

Referring to FIG. 34, instead of pulling the ends 502, 504 through the bight 508, the first end 502 has been pulled through the material 510 by pulling on one side of the bight 508 to form a simple stitch 514.

Figure 35:
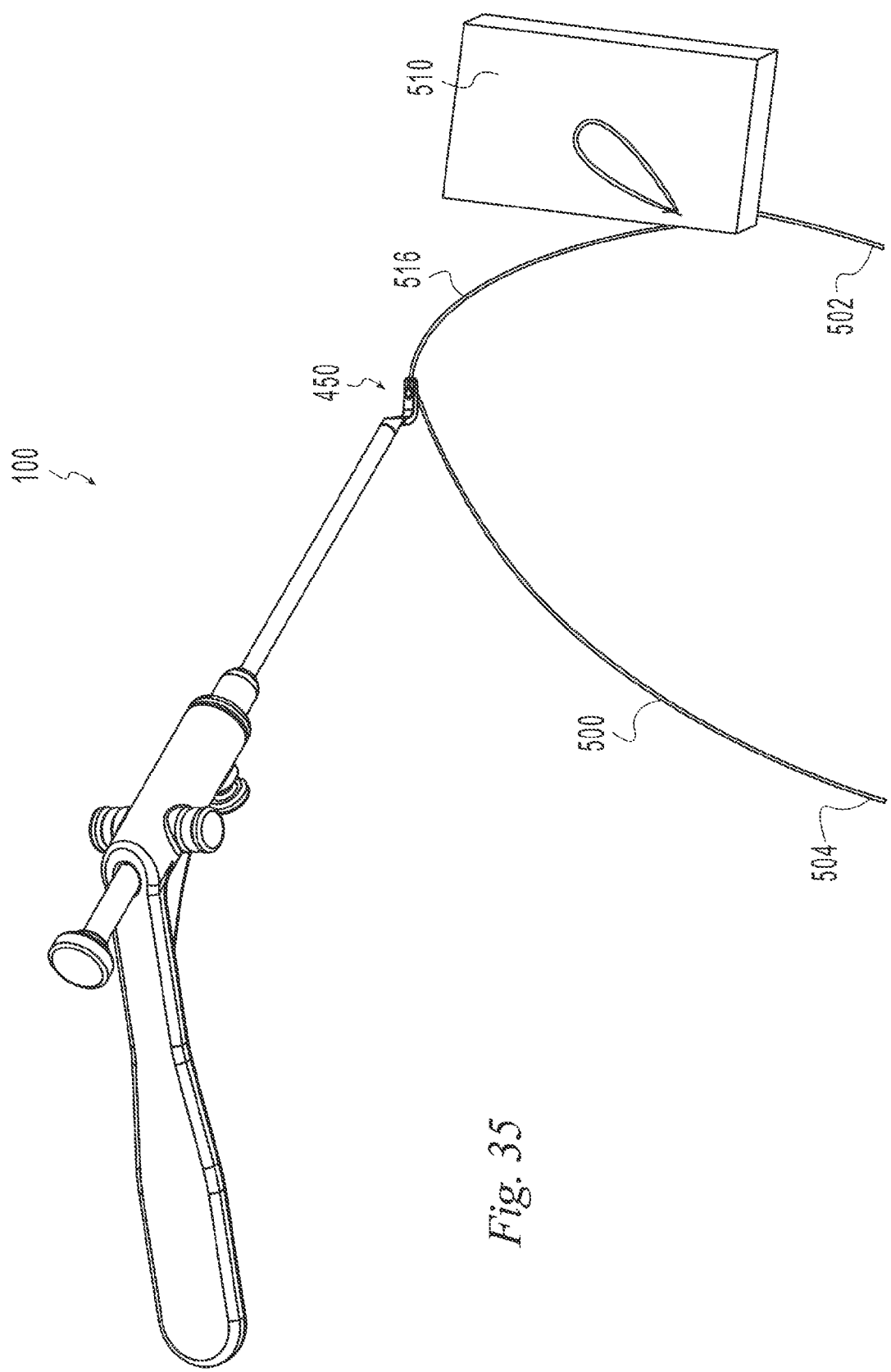
Figure 36:
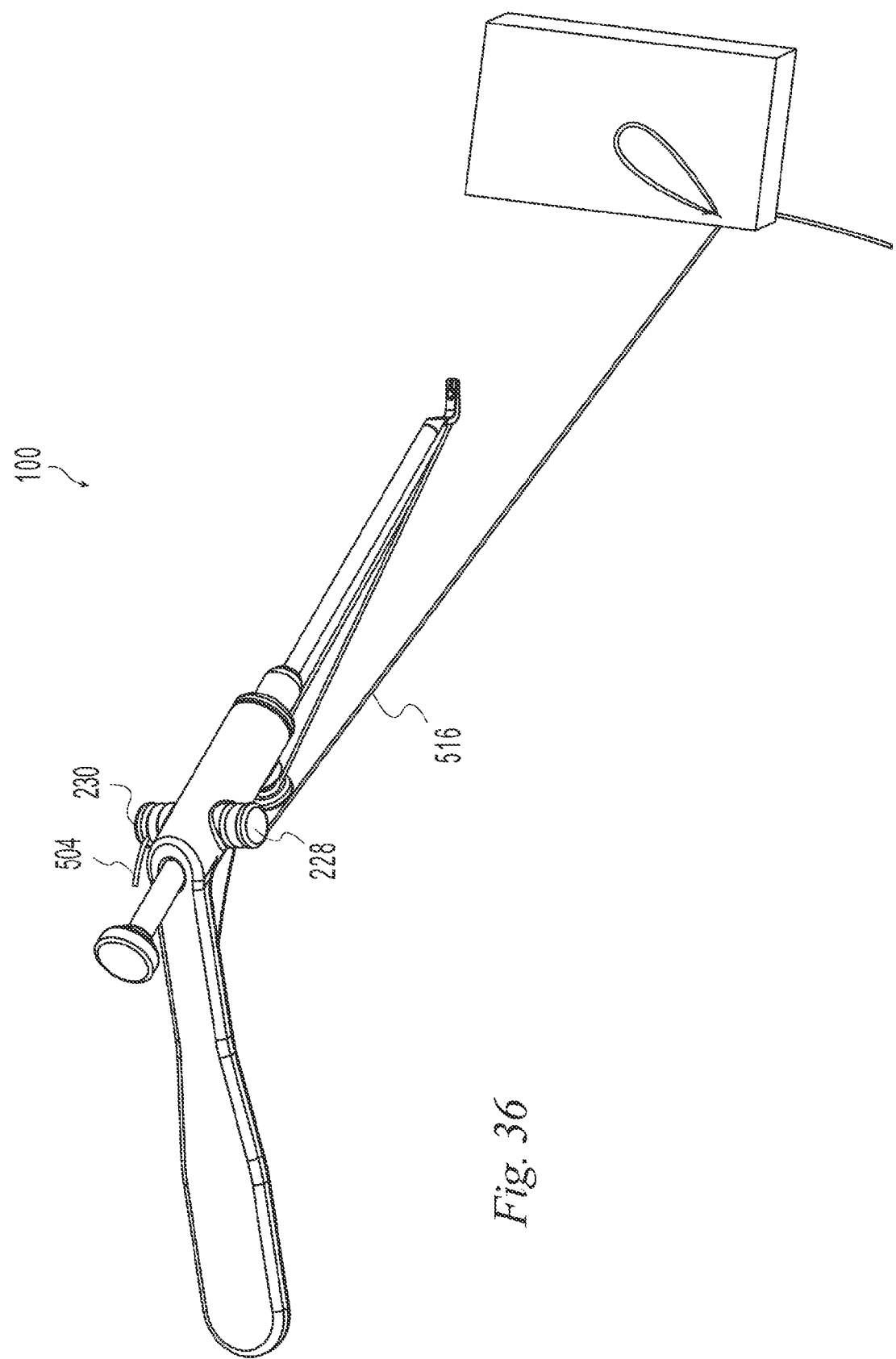
Figure 37:
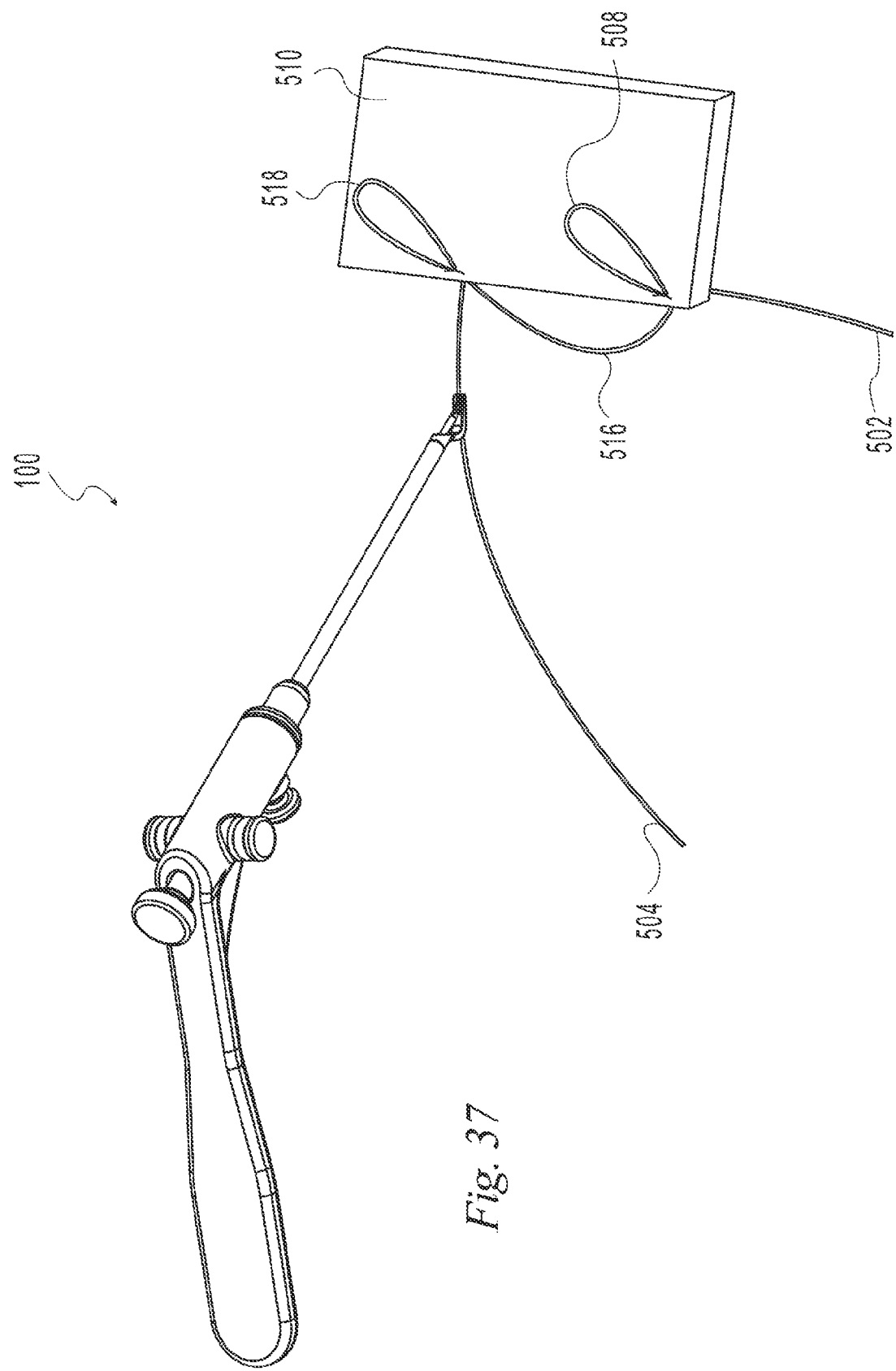

Referring to FIG. 35, the passer 100 is prepared for making a running stitch by pulling suture 500 distally through the foot to create slack 516 between the foot 450 and material 510. Referring to FIG. 36, the slack 516 and the second end 504 have been pulled proximally and secured to the knobs 228, 230. Referring to FIG. 37 a second bight 518 has been passed through the material 510 in the same manner as the first bight 508 and the slack 516 and second end 504 have been released from the passer 100.

Figure 38:
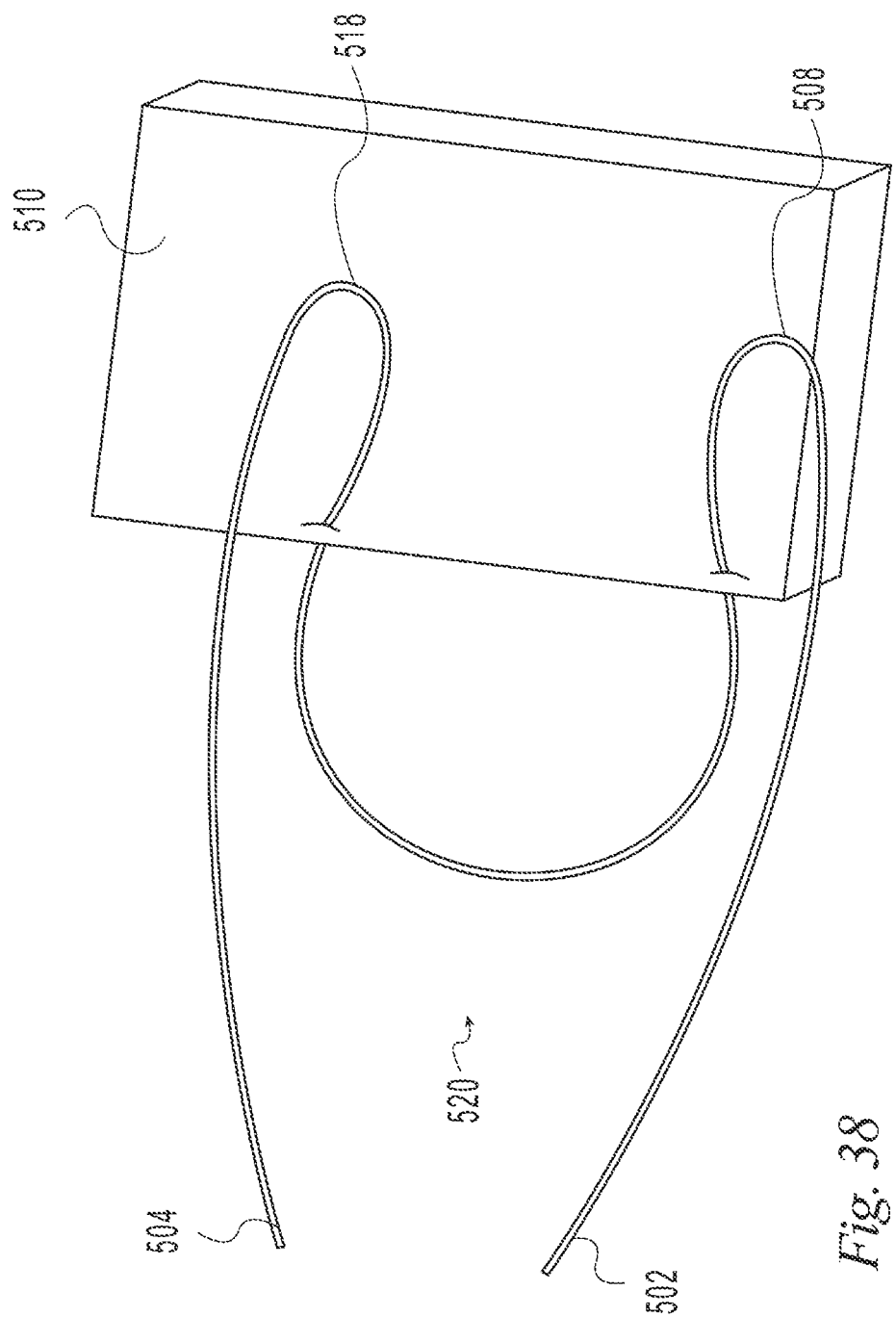

Referring to FIG. 38, the first and second ends 502, 504 have been pulled through to the front side of the material 510 by pulling on one side of each of the bights 508, 518 to form a mattress stitch 520 in the material 510.

Figure 39:
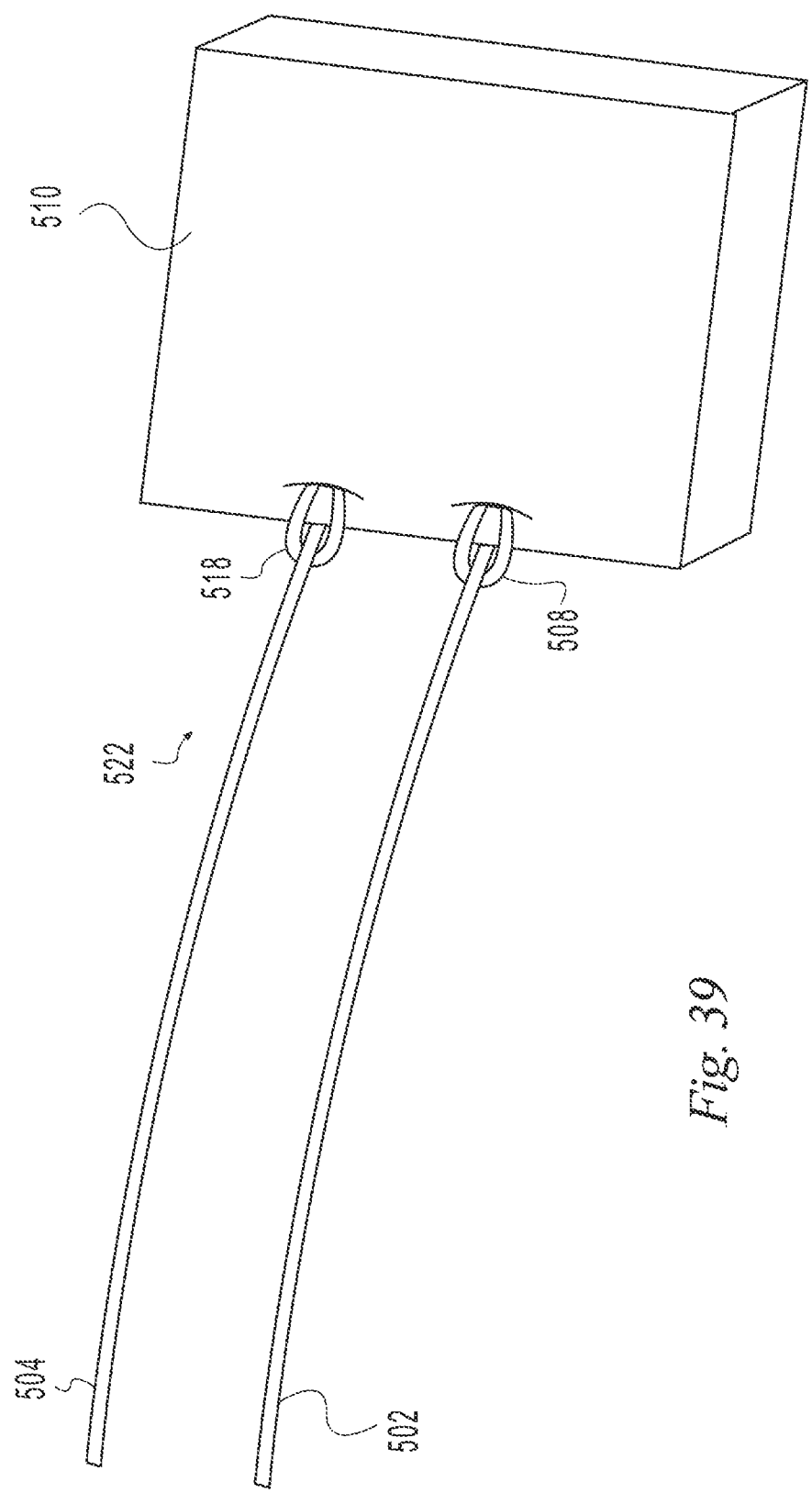

Referring to FIG. 39, instead of the ends 502, 504 being pulled through the material the first end 502 has been placed through the first bight 508 and the second end 504 has been placed through the second bight 518 to form a modified mattress stitch 522 with each end 502, 504 secured by a hitch.

Figure 40:
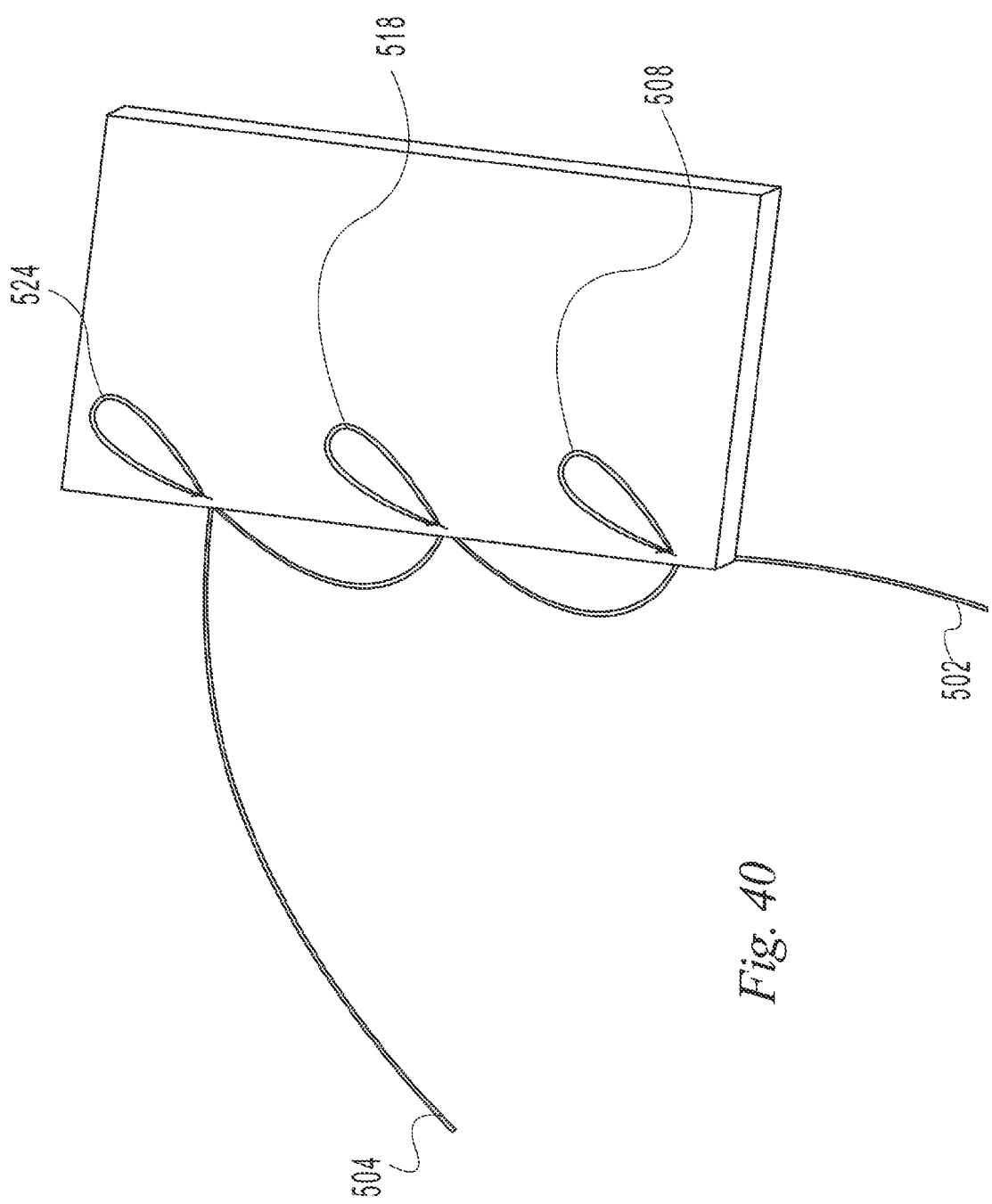
Figure 41:
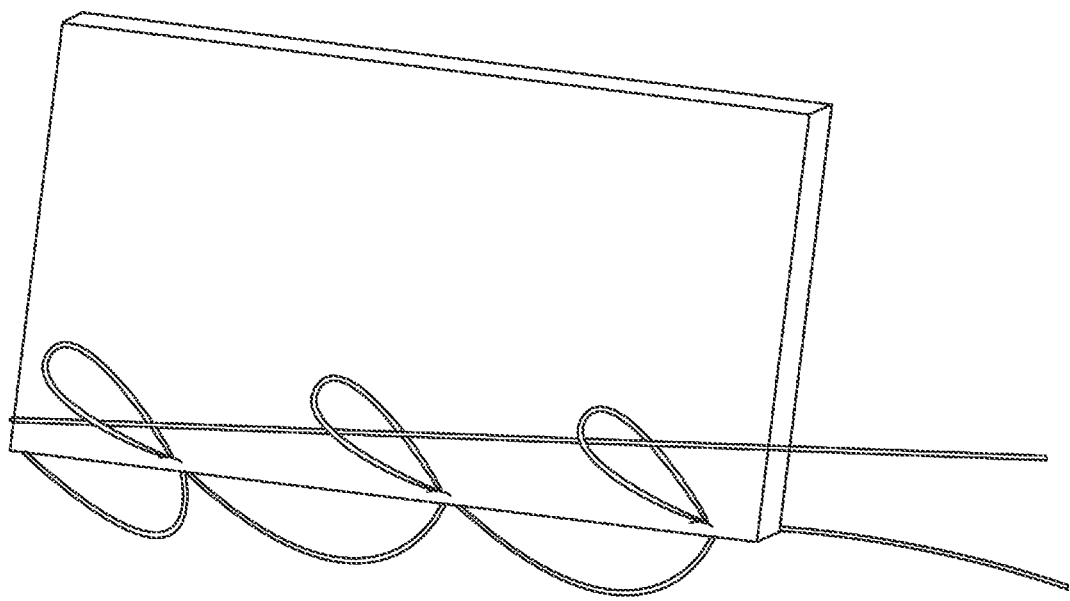

Referring to FIG. 40, a third bight 524 has been pulled through the material in the same manner as the first two bights 508, 518. A stitch may be formed by placing one or both ends 502, 504 through the bights 508, 518, 524 to lock the bights as shown in FIG. 41.

Figure 42:
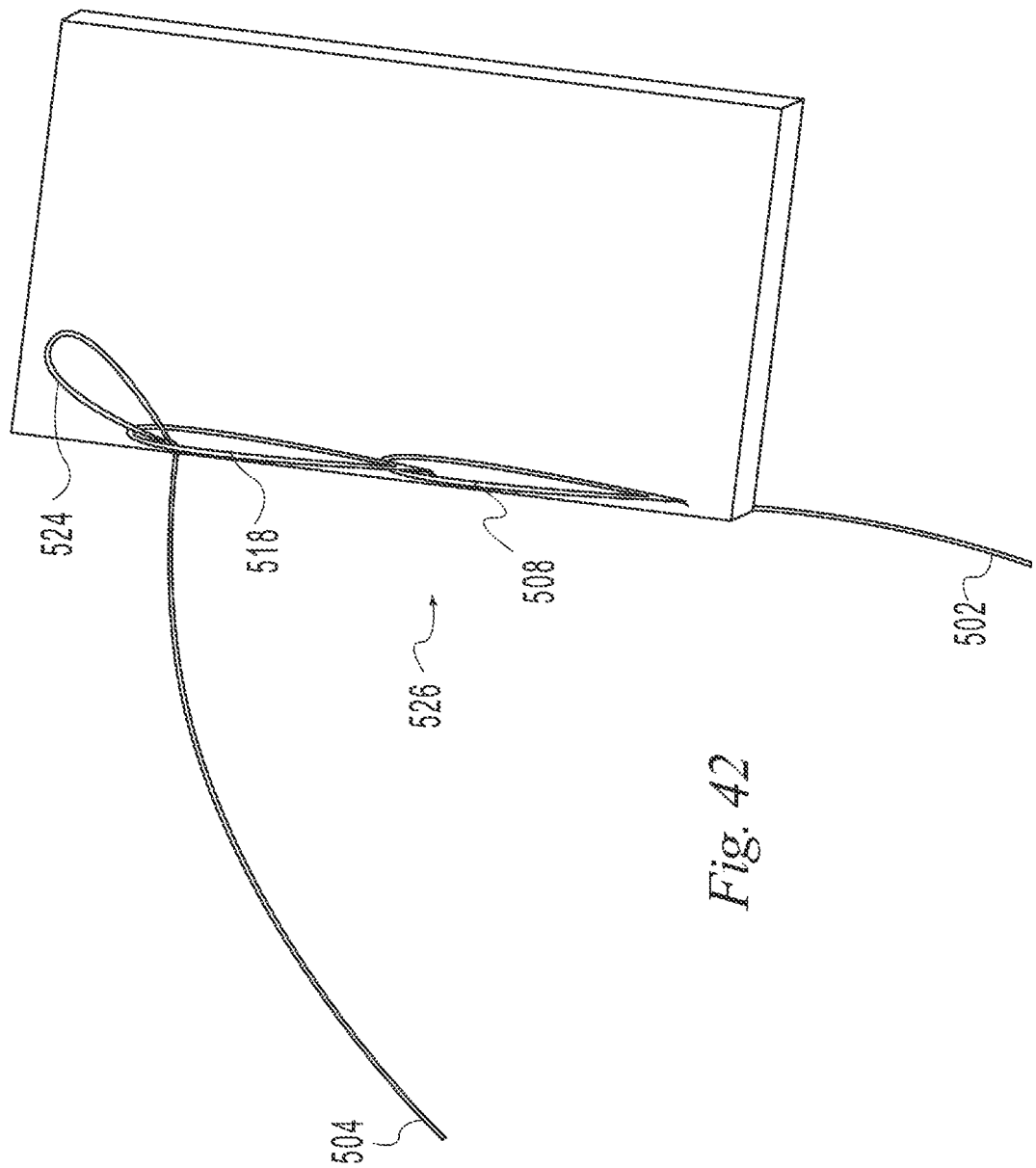

Referring to FIG. 42, instead of placing the ends through the bights, the second bight 518 has been looped through the first bight 508, and the third bight 524 has been looped through the second bight 518 to form a chain stitch 526.

Figure 43:
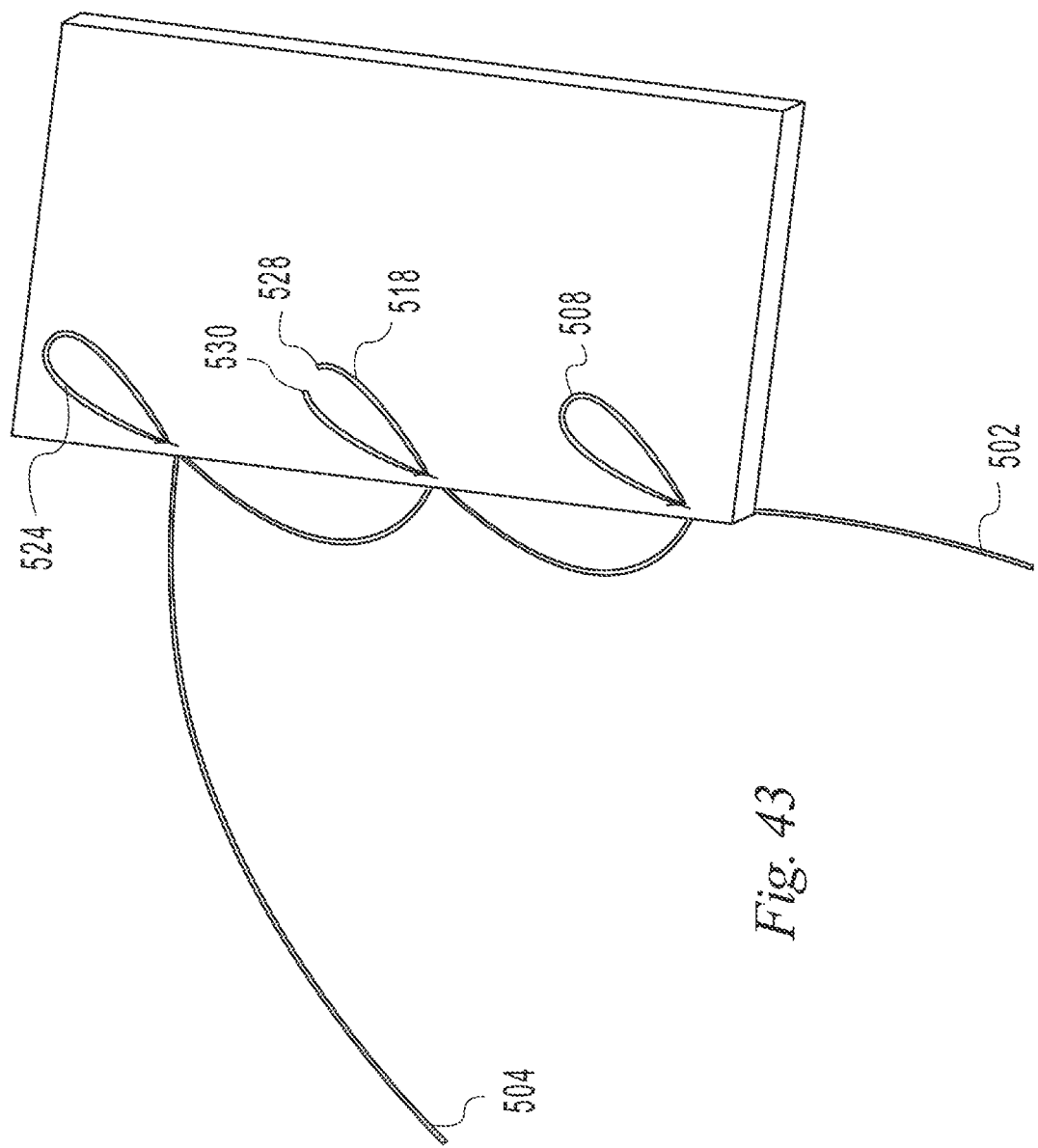
Figure 44:
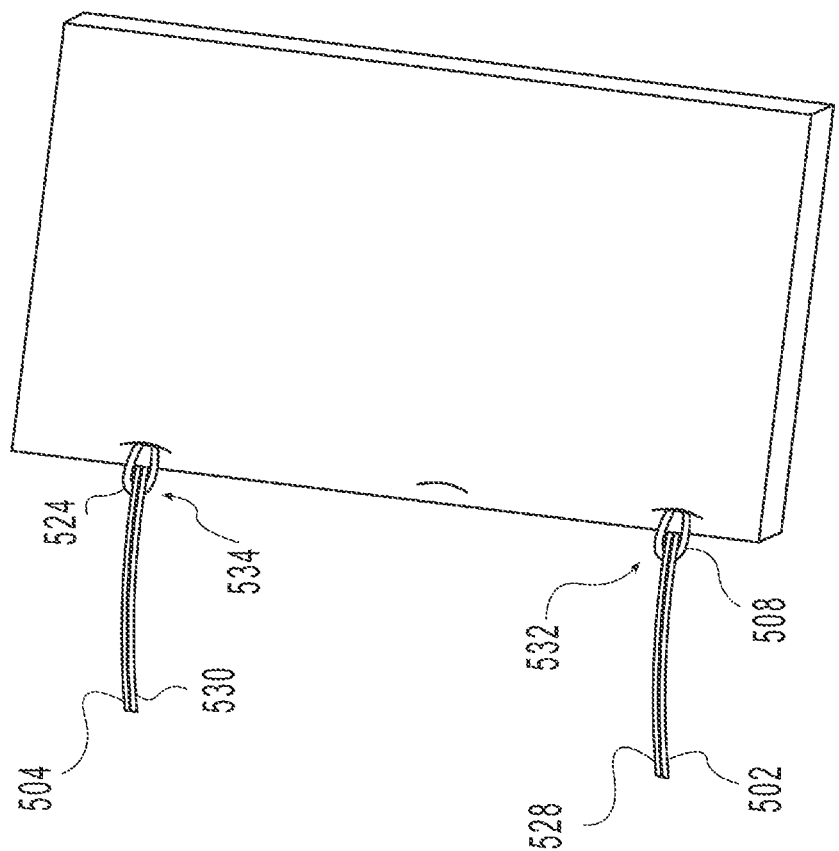

Referring to FIGS. 43 and 44, another alternative to forming stitches with three bights is shown. Here, the second bight 518 has been cut to form third and fourth ends 528, 530. The third and fourth ends 528, 530 are pulled back through the material 510 and then the first and third ends 502, 528 are placed through the first bight 508 to form a first hitch 532 and the second and fourth ends 504, 530 are placed through the third bight 524 to form a second hitch 534.

Alternatively, as shown in FIGS. 45 and 46, the same construct could be produced by forming two bights 508, 518, and cutting through the slack 536 on the back side of the material 510 to produce third and fourth ends 538, 540 which with the first and second ends 502, 504 are used to form hitches 542, 544.

Illustrative examples of instruments and methods have been shown in use to pass suture through material to form illustrative hitches. The present invention is not limited to the specific instruments and methods depicted. Furthermore, it is to be understood that instruments and methods according to the present invention may be used to pass any number of bights of suture through one or more materials and form any desirable construct.

What is claimed is:

1. A suture passer for passing a suture, the suture passer comprising:

a housing defining a linear motion axis extending proximally to distally;

a needle mounted for translation along the motion axis between a first proximal position and a second distal position; and a foot mounted to the housing, the foot includes an elbow having a proximal portion and a distal portion, the proximal portion having a distal facing surface extending along a proximal portion axis diverging distally away from the motion axis, the proximal portion axis forming an angle relative to the motion axis, the distal portion extending distally from the proximal portion, the distal portion has a proximal facing surface and a distal surface, the proximal facing surface and the distal surface positioned on opposite sides of the distal portion, the proximal facing surface extending along a distal portion axis crossing the motion axis, the distal portion further comprising a groove extending distally in the proximal facing surface and not through the distal surface, and a foot notch formed through the proximal facing surface and the distal surface at a distal end of the foot, the foot notch in communication with the groove, the distal portion including an eye in the proximal facing surface coaxial with the motion axis and able to receive the needle in the second position, the distal portion axis forming an angle in the range of 0 to 90 degrees relative to the motion axis, and the distal portion including a hole that extends through the distal surface about a hole axis and intersects the eye, wherein the hole axis forms an angle in a range of 45 to 135 degrees relative to the motion axis.

2. The suture passer of claim 1 wherein the angle between the distal portion axis and the motion axis is in the range of 25 to 55 degrees.

3. The suture passer of claim 2 wherein the angle between the distal portion axis and the motion axis is in the range of 35 to 45 degrees.

4. The suture passer of claim 1 wherein the distal portion terminates in the distal end, the hole axis intersects the eye at a location that is adjacent to a proximal aspect of the eye, the groove in the proximal facing surface is adjacent to the hole, wherein the hole, groove and notch are aligned to receive the suture through the distal portion, across the eye, along the groove in the proximal facing surface, and around the distal end.

5. The suture passer of claim 1 wherein the proximal facing surface of the distal portion defines a plane and the needle further comprises a shaft having a notch formed therein, the notch crossing the plane defined by the proximal facing surface as the needle moves between the first and second positions, the notch being operable to engage the suture in the second position and impart a proximally directed force on the suture as the needle moves toward the first position.

6. The suture passer of claim 5 wherein the notch extends into the needle shaft at a notch angle relative to the motion axis, the notch having an opening at a surface of the needle shaft, the opening facing generally proximally, the notch angle being in the range of 35 to 55 degrees.

7. The suture passer of claim 5 wherein the shaft has a first side surface, the notch being formed into the first side surface, the shaft tapering distally to define a bevel on the first side surface distal to the notch, the bevel being operable to engage the suture as the needle is moved to the second position.

8. The suture passer of claim 1, wherein the proximal portion axis forms an angle in the range of 0 to 90 degrees relative to the motion axis.

9. The suture passer of claim 8 wherein the angle between the proximal portion axis and the motion axis is in the range of 25 to 55 degrees.

10. The suture passer of claim 9 wherein the angle between the proximal portion axis and the motion axis is in the range of 35 to 45 degrees.

11. A suture passer comprising:
a housing defining a linear motion axis extending proximally to distally;
a needle mounted coaxial with the motion axis for axial translation between a first proximal position and a second distal position, the needle remaining coaxial with the motion axis throughout its range of motion; and
a foot mounted to the housing, the foot includes an elbow having a proximal portion and a distal portion, the proximal portion having a distal facing surface extending along a proximal portion axis diverging distally away from the motion axis, the proximal portion axis forming a non-perpendicular angle relative to the motion axis, the distal portion extending distally from the proximal portion, the distal portion has a proximal facing surface extending along a distal portion axis crossing the motion axis and a distal surface, the distal surface and the proximal facing surface positioned on opposite sides of the distal portion, the distal portion including an eye in the proximal facing surface, the eye having an eye axis coaxial with the motion axis and able to receive the needle in the second position, and the distal portion including a hole that extends through the distal surface and intersects the eye, wherein the hole has a hole axis that forms an angle in a range of 45 to 135 degrees relative to the motion axis;
wherein the distal portion terminates in a distal end, the hole is adjacent to a proximal aspect of the eye, the distal portion includes a groove extending distally in the proximal facing surface adjacent the hole, and the distal portion includes a foot notch in the distal end adjacent the groove, wherein the hole, groove and notch are aligned and operable to receive a suture through the distal portion, across the eye, along the groove in the proximal facing surface, and around the distal end.

12. The suture passer of claim 11 wherein the distal portion axis forms an angle in the range of 0 to 90 degrees relative to the motion axis.

13. The suture passer of claim 12 wherein the angle between the distal portion axis and the motion axis is in the range of 25 to 55 degrees.

14. The suture passer of claim 13 wherein the angle between the distal portion axis and the motion axis is in the range of 35 to 45 degrees.

15. The suture passer of claim 11 wherein the proximal portion axis forms an angle in the range of 0 to 90 degrees relative to the motion axis.

16. The suture passer of claim 15 wherein the angle between the proximal portion axis and the motion axis is in the range of 25 to 55 degrees.

17. The suture passer of claim 16 wherein the angle between the proximal portion axis and the motion axis is in the range of 35 to 45 degrees.

18. A suture passer comprising:
a housing defining a linear motion axis extending proximally to distally
a needle mounted coaxial with the motion axis for axial translation between a first proximal position and a second distal position, the needle remaining coaxial with the motion axis throughout its range of motion; and
a foot mounted to the housing, the foot includes an elbow having a proximal portion and a distal portion, the proximal portion having a distal facing surface, the distal portion extending distally from the proximal portion, the distal portion has a proximal facing surface and a distal surface, the proximal facing surface and the distal facing surface positioned on opposite sides of the distal portion, the distal portion including an eye in the proximal facing surface, the eye having an eye axis coaxial with the motion axis and able to receive the needle in the second position, and the distal portion including a hole that extends through the distal surface and intersects the eye, wherein the hole has a hole axis that forms an angle in a range of 45 to 135 degrees relative to the motion axis;
wherein the distal portion terminates in a distal end, the hole is adjacent to a proximal aspect of the eye, the distal portion includes a groove extending distally in the proximal facing surface adjacent the hole, and the distal portion includes a foot notch in the distal end adjacent the groove, wherein the hole, groove and notch are aligned and operable to receive a suture through the distal portion, across the eye, along the groove in the proximal facing surface, and around the distal end.

19. The suture passer of claim 18 wherein the distal facing surface extends along a proximal portion axis diverging distally away from the motion axis and the proximal facing surface extends along a distal portion axis crossing the motion axis.

20. The suture passer of claim 19 wherein the distal portion axis forms an angle in the range of 0 to 90 degrees relative to the motion axis.

21. The suture passer of claim 20 wherein the angle between the distal portion axis and the motion axis is in the range of 25 to 55 degrees.

22. The suture passer of claim 21 wherein the angle between the distal portion axis and the motion axis is in the range of 35 to 45 degrees.

23. The suture passer of claim 19 wherein the proximal portion axis forms an angle in the range of 0 to 90 degrees relative to the motion axis.

24. The suture passer of claim 23 wherein the angle between the proximal portion axis and the motion axis is in the range of 25 to 55 degrees.

25. The suture passer of claim 24 wherein the angle between the proximal portion axis and the motion axis is in the range of 35 to 45 degrees.

\* \* \* \* \*